(12) United States Patent
Diamond

(10) Patent No.: US 9,758,557 B2
(45) Date of Patent: Sep. 12, 2017

(54) C1Q PEPTIDES AND USES THEREOF

(71) Applicant: THE FEINSTEIN INSTITUTE FOR MEDICAL RESEARCH, Manhasset, NY (US)

(72) Inventor: Betty A. Diamond, Bronx, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 14/331,301

(22) Filed: Jul. 15, 2014

(65) Prior Publication Data
US 2015/0104472 A1   Apr. 16, 2015

Related U.S. Application Data

(60) Provisional application No. 61/847,235, filed on Jul. 17, 2013.

(51) Int. Cl.
*A61K 38/00* (2006.01)
*C07K 14/47* (2006.01)

(52) U.S. Cl.
CPC .......... *C07K 14/4713* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 6,001,964 A | 12/1999 | Gaynor et al. | |
| 6,932,970 B1 * | 8/2005 | Gaynor | C07K 7/06 424/185.1 |
| 8,962,807 B2 * | 2/2015 | Verdonck | G01N 33/6854 530/387.3 |

FOREIGN PATENT DOCUMENTS

| WO | 2005037301 A1 | 4/2005 |
| WO | WO 2011073180 | * 6/2011 |

OTHER PUBLICATIONS

Sellar G C et al., entitled "Characterization and organization of the genes encoding the A-, B- and C-chains of human complement subcomponent C1q," Biochem. J. (1991) 274, 481-490.
Gaynor B et al., entitled "Peptide inhibition of glomercular deposition of an anti-DNA antibody," Proc. Natl. Acad. Sci., vol. 94, pp. 1955-1960.

* cited by examiner

*Primary Examiner* — Thomas S Heard
(74) *Attorney, Agent, or Firm* — Amster, Rothstein & Ebenstein LLP

(57) ABSTRACT

Isolated C1q peptides, fusion proteins and compositions comprising such and fusion proteins comprising are provided. Isolated fusion proteins comprising $X_4WX_5YX_6$ as defined herein and compositions comprising such are also provided. Methods of treating autoimmune disorders are provided.

3 Claims, 3 Drawing Sheets

C1Q PEPTIDES AND USES THEREOF

CROSS-REFERENCE TO RELATED APPLICATIONS

This application claims benefit of U.S. Provisional Application No. 61/847,235, filed Jul. 17, 2013, the contents of which are hereby incorporated by reference.

BACKGROUND OF THE INVENTION

Throughout this application various publications are referred to in square brackets. Full citations for these references may be found at the end of the specification immediately preceding the claims. The disclosures of these publications are hereby incorporated by reference in their entireties into the subject application to more fully describe the art to which the subject application pertains.

Systemic lupus erythematosus (SLE) is an autoimmune disorder primarily affecting women during their reproductive years. It is characterized by activation of autoreactive B cells with ensuing elevation in serum autoantibody titers. Autoantibodies against nuclear antigens are found in 95% or more of lupus patients; antibodies to doublestranded (ds) DNA are present in approximately 70% of patients. Titers of anti-dsDNA antibodies correlate with disease activity are most common in patients with renal disease and can be isolated from glomeruli of patients with lupus nephritis [1, 2]. Indeed, many anti-dsDNA antibodies cross-react with glomerular antigens. Clinical involvement of the kidneys occurs in 50 to 80% of lupus patients during the course of their disease and renal pathology is found in as many as 90% of patients at autopsy [3].

More recently, it has been demonstrated that lupus patients with anti-DNA or anti-RNP antibodies experience systemic inflammation as well as discrete target organ injury, with increased expression of type I interferon (IFN) inducible genes in peripheral blood mononuclear cells. This appears to result from activation of plasmacytoid dendritic cells (pDCs) and secretion of IFN, mediated in part by nucleic acid-containing immune complexes (IC) that are internalized by activating Fc receptors (FcRs) and subsequently engage toll-like receptors (TLRs) that recognize nucleic acid ligands or even solely by engaging activating FcRs [4, 5].

C1q is a 460 KDa protein formed by 6 homotrimeric subunits containing a N-terminal collagen-like sequence and a C-terminal globular region. It functions in the innate immune response to clear pathogens by activation of the classical complement cascade [6]. Moreover, it contributes to the clearance of IC and apoptotic cells from the circulation, an activity which is important for maintenance of immune tolerance to self antigens [7]. C1q has also been found to inhibit monocyte to DC differentiation and DC activation and therefore may also play a central role in preventing an aberrant adaptive immune response [8, 9]. Although C1q deficiency is a rare phenomenon, it provides the strongest genetic risk for lupus [10]. Several receptors binding C1q have been identified in various cell types including C1qRp (CD93); cC1qR (calreticulin), CR1 and CD35 which bind the collagen region of C1q; gC1qR (multiligand binding receptor) which binds to the globular domain of C1q; and C1qR02 [11]. Engagement of each of these receptors appears to initiate distinct cellular functions; for example, engagement of C1qRp enhances phagocytosis while engagement of C1qR02 triggers a superoxide burst in neutrophils. Most importantly for an understanding of SLE, absence of C1q has been shown to lead to enhanced IFNα production by both human and murine pDCs [12,13].

The present invention addresses the need for improved therapies, based on C1q, to combat autoimmune conditions, including lupus.

SUMMARY OF THE INVENTION

This invention provides an isolated peptide of 5 to 20 consecutive amino acid residues in length comprising the sequence $EAX_1X_2X_3$ (SEQ ID NO:1), wherein $X_1$ is D or G, wherein $X_2$ is S or R or Y, and wherein $X_3$ is V or P or I or G.

This invention also provides a fusion protein comprising the isolated peptide as described joined at an N-terminal amino acid or C-terminal amino acid thereof by a peptide bond to a second peptide or polypeptide or protein.

A composition is provided comprising the isolated peptide or the fusion protein.

A fusion protein is also provided comprising an isolated peptide of 5 to 20 consecutive amino acid residues in length comprising the sequence $X_4WX_5YX_6$ (SEQ ID NO:6), wherein $X_4$ is D or E, wherein $X_5$ is D or E, and wherein $X_6$ is G or S, joined at an N or C terminal amino acid thereof by a peptide bond to a second peptide or polypeptide or protein. A composition is provided comprising the fusion protein.

A method of treating an autoimmune condition in a subject is also provided, the method comprising administering to the subject the isolated peptide, the fusion protein, or the composition, as described herein, in an amount effective to treat an autoimmune condition in a subject.

A method of treating an autoimmune condition in a subject is also provided, the method comprising administering to the subject the isolated peptide, the fusion protein, or the composition, as described herein, in an amount effective to reduce circulating autoantibodies in a subject and thereby treat an autoimmune condition.

DETAILED DESCRIPTION OF THE INVENTION

Figures 1A, 1B, 1C, 1D:
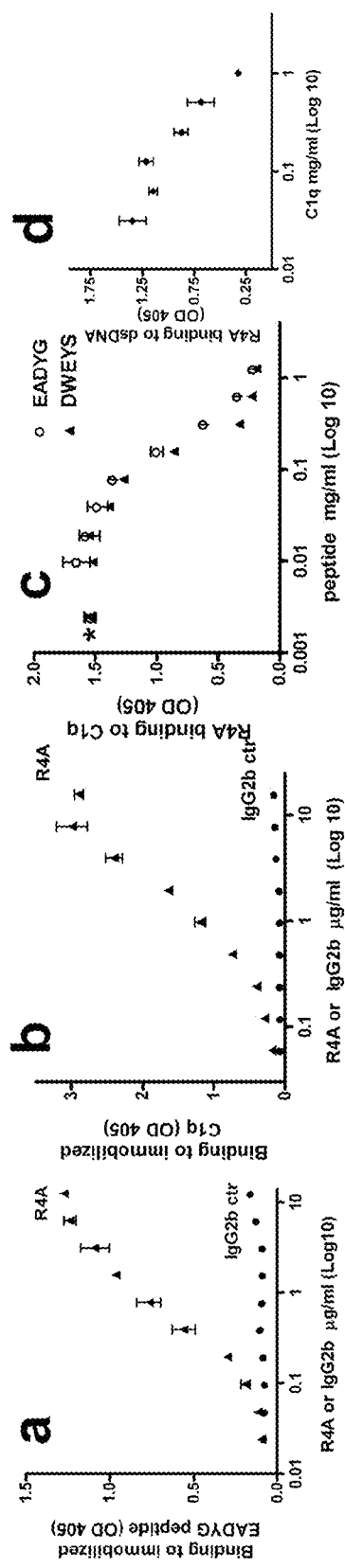
FIG. 1A-1G. Cross reactivity of R4A. 1A. R4A binds to EADYG peptide. 1B. R4A binds to C1q. 1C. Inhibition of R4A binding to C1q by DWEYS or EADYG peptide. 1D. Inhibition of R4A binding to dsDNA by C1q. 1E. R4A binds to C1q (solid line) but does not bind to isolated collagen tail of C1q (dotted line). 1F. R4A binding to isolated glomeruli. DAPI was used to visualize DNA in the glomeruli. Results are representative of three different experiments. 1g. R4A binding to kidney is significantly less in the absence of C1q. Combined three separate experiments and relative IDV represents percent IDV signal within each experiment.

This invention provides an isolated peptide of 5 to 20 consecutive amino acid residues in length comprising the sequence EAX$_1$X$_2$X$_3$ (SEQ ID NO:1), wherein X$_1$ is D or G, wherein X$_2$ is S or R or Y, and wherein X$_3$ is V or P or I or G.

In an embodiment, X$_1$ is D or G, X$_2$ is S or R, and X$_3$ is V or P. In a preferred embodiment, the isolated peptide comprises the sequence EADSV (SEQ ID NO:2). In an embodiment, the isolated peptide comprises the sequence EAGRP (SEQ ID NO:3). In an embodiment, the isolated peptide comprises the sequence EADYG (SEQ ID NO:4). In an embodiment, the isolated peptide comprises the sequence EADSI (SEQ ID NO:5).

The 5 to 20 consecutive amino acid isolated peptide can have a sequence identical to a 5 to 20 amino acid residue portion, respectively, of a human C1q. In an embodiment, the human C1q comprises SEQ ID NO:6. In an embodiment, the isolated peptide does not comprise the remaining portions(s) of a human C1q.

The 5 to 20 consecutive amino acid isolated peptide can be any one of 20, 19, 18, 17, 16, 15, 14, 13, 12, 11, 10, 9, 8, 7, 6 or 5 amino acids in length. Each individual peptide length recited herein is encompassed within the invention as an individual embodiment. In addition, each of all the length ranges within the recited lengths is also encompassed within the invention as an individual embodiment. For example, this invention encompasses the isolated peptides of 15-20 amino acids in length, the isolated peptides of 14-20 amino acids in length, the isolated peptides of 14-19 amino acids in length, the isolated peptides of 13-14 amino acids in length and so forth.

The isolated peptide can have one of the following sequences:

```
EADSVF                    (SEQ ID NO: 7)
EADSVFS                   (SEQ ID NO: 8)
EADSVFSG                  (SEQ ID NO: 9)
EADSVFSGF                 (SEQ ID NO: 10)
EADSVFSGFL                (SEQ ID NO: 11)
EADSVFSGFLI               (SEQ ID NO: 12)
EADSVFSGFLIF              (SEQ ID NO: 13)
EADSVFSGFLIFP             (SEQ ID NO: 14)
EADSVFSGFLIFPS            (SEQ ID NO: 15)
EADSVFSGFLIFPSA           (SEQ ID NO: 16)
WVEKDPKKGHIYQGSEADSV      (SEQ ID NO: 17)
VEKDPKKGHIYQGSEADSV       (SEQ ID NO: 18)
EKDPKKGHIYQGSEADSV        (SEQ ID NO: 19)
KDPKKGHIYQGSEADSV         (SEQ ID NO: 20)
DPKKGHIYQGSEADSV          (SEQ ID NO: 21)
PKKGHIYQGSEADSV           (SEQ ID NO: 22)
KKGHIYQGSEADSV            (SEQ ID NO: 23)
KGHIYQGSEADSV             (SEQ ID NO: 24)
GHIYQGSEADSV              (SEQ ID NO: 25)
HIYQGSEADSV               (SEQ ID NO: 26)
IYQGSEADSV                (SEQ ID NO: 27)
YQGSEADSV                 (SEQ ID NO: 28)
QGSEADSV                  (SEQ ID NO: 29)
GSEADSV                   (SEQ ID NO: 30)
SEADSV                    (SEQ ID NO: 31)
VEKDPKKGHIYQGSEADSVF      (SEQ ID NO: 32)
EKDPKKGHIYQGSEADSVFS      (SEQ ID NO: 33)
KDPKKGHIYQGSEADSVFSG      (SEQ ID NO: 34)
DPKKGHIYQGSEADSVFSGF      (SEQ ID NO: 35)
PKKGHIYQGSEADSVFSGFL      (SEQ ID NO: 36)
KKGHIYQGSEADSVFSGFLI      (SEQ ID NO: 37)
KGHIYQGSEADSVFSGFLIF      (SEQ ID NO: 38)
GHIYQGSEADSVFSGFLIFP      (SEQ ID NO: 39)
HIYQGSEADSVFSGFLIFPS      (SEQ ID NO: 40)
IYQGSEADSVFSGFLIFPSA      (SEQ ID NO: 41)
EKDPKKGHIYQGSEADSVF       (SEQ ID NO: 42)
KDPKKGHIYQGSEADSVFS       (SEQ ID NO: 43)
DPKKGHIYQGSEADSVFSG       (SEQ ID NO: 44)
PKKGHIYQGSEADSVFSGF       (SEQ ID NO: 45)
KKGHIYQGSEADSVFSGFL       (SEQ ID NO: 46)
KGHIYQGSEADSVFSGFLI       (SEQ ID NO: 47)
GHIYQGSEADSVFSGFLIF       (SEQ ID NO: 48)
HIYQGSEADSVFSGFLIFP       (SEQ ID NO: 49)
IYQGSEADSVFSGFLIFPS       (SEQ ID NO: 50)
YQGSEADSVFSGFLIFPSA       (SEQ ID NO: 51)
DPKKGHIYQGSEADSVF         (SEQ ID NO: 52)
PKKGHIYQGSEADSVFS         (SEQ ID NO: 53)
KKGHIYQGSEADSVFSG         (SEQ ID NO: 54)
KGHIYQGSEADSVFSGF         (SEQ ID NO: 55)
GHIYQGSEADSVFSGFL         (SEQ ID NO: 56)
HIYQGSEADSVFSGFLI         (SEQ ID NO: 57)
IYQGSEADSVFSGFLIF         (SEQ ID NO: 58)
YQGSEADSVFSGFLIFP         (SEQ ID NO: 59)
QGSEADSVFSGFLIFPS         (SEQ ID NO: 60)
GSEADSVFSGFLIFPSA         (SEQ ID NO: 61)
PKKGHIYQGSEADSVF          (SEQ ID NO: 62)
KKGHIYQGSEADSVFS          (SEQ ID NO: 63)
KGHIYQGSEADSVFSG          (SEQ ID NO: 64)
GHIYQGSEADSVFSGF          (SEQ ID NO: 65)
HIYQGSEADSVFSGFL          (SEQ ID NO: 66)
IYQGSEADSVFSGFLI          (SEQ ID NO: 67)
YQGSEADSVFSGFLIF          (SEQ ID NO: 68)
QGSEADSVFSGFLIFP          (SEQ ID NO: 69)
GSEADSVFSGFLIFPS          (SEQ ID NO: 70)
SEADSVFSGFLIFPSA          (SEQ ID NO: 71)
KKGHIYQGSEADSVF           (SEQ ID NO: 72)
KGHIYQGSEADSVFS           (SEQ ID NO: 73)
GHIYQGSEADSVFSG           (SEQ ID NO: 74)
HIYQGSEADSVFSGF           (SEQ ID NO: 75)
IYQGSEADSVFSGFL           (SEQ ID NO: 76)
YQGSEADSVFSGFLI           (SEQ ID NO: 77)
QGSEADSVFSGFLIF           (SEQ ID NO: 78)
GSEADSVFSGFLIFP           (SEQ ID NO: 79)
SEADSVFSGFLIFPS           (SEQ ID NO: 80)
EADSVFSGFLIFPSA           (SEQ ID NO: 81)
GHIYQGSEADSVF             (SEQ ID NO: 82)
HIYQGSEADSVFS             (SEQ ID NO: 83)
IYQGSEADSVFSG             (SEQ ID NO: 84)
YQGSEADSVFSGF             (SEQ ID NO: 85)
QGSEADSVFSGFL             (SEQ ID NO: 86)
GSEADSVFSGFLI             (SEQ ID NO: 87)
SEADSVFSGFLIF             (SEQ ID NO: 88)
EADSVFSGFLIFP             (SEQ ID NO: 89)
HIYQGSEADSVF              (SEQ ID NO: 90)
IYQGSEADSVFS              (SEQ ID NO: 91)
YQGSEADSVFSG              (SEQ ID NO: 92)
QGSEADSVFSGF              (SEQ ID NO: 93)
GSEADSVFSGFL              (SEQ ID NO: 94)
SEADSVFSGFLI              (SEQ ID NO: 95)
EADSVFSGFLIF              (SEQ ID NO: 96)
IYQGSEADSVF               (SEQ ID NO: 97)
YQGSEADSVFS               (SEQ ID NO: 98)
QGSEADSVFSG               (SEQ ID NO: 99)
GSEADSVFSGF               (SEQ ID NO: 100)
SEADSVFSGFL               (SEQ ID NO: 101)
EADSVFSGFLI               (SEQ ID NO: 102)
YQGSEADSVF                (SEQ ID NO: 103)
QGSEADSVFS                (SEQ ID NO: 104)
GSEADSVFSG                (SEQ ID NO: 105)
SEADSVFSGF                (SEQ ID NO: 106)
EADSVFSGFL                (SEQ ID NO: 107)
QGSEADSVF                 (SEQ ID NO: 108)
GSEADSVFS                 (SEQ ID NO: 109)
SEADSVFSG                 (SEQ ID NO: 110)
EADSVFSGF                 (SEQ ID NO: 111)
GSEADSVF                  (SEQ ID NO: 112)
SEADSVFS                  (SEQ ID NO: 113)
EADSVFSG                  (SEQ ID NO: 114)
SEADSVF                   (SEQ ID NO: 115)
EADSVFS                   (SEQ ID NO: 116)
MVTEDLCRAPDGKKGEAGRP      (SEQ ID NO: 117)
VTEDLCRAPDGKKGEAGRP       (SEQ ID NO: 118)
TEDLCRAPDGKKGEAGRP        (SEQ ID NO: 119)
EDLCRAPDGKKGEAGRP         (SEQ ID NO: 120)
DLCRAPDGKKGEAGRP          (SEQ ID NO: 121)
LCRAPDGKKGEAGRP           (SEQ ID NO: 122)
CRAPDGKKGEAGRP            (SEQ ID NO: 123)
RAPDGKKGEAGRP             (SEQ ID NO: 124)
APDGKKGEAGRP              (SEQ ID NO: 125)
PDGKKGEAGRP               (SEQ ID NO: 126)
DGKKGEAGRP                (SEQ ID NO: 127)
GKKGEAGRP                 (SEQ ID NO: 128)
```

```
KKGEAGRP               (SEQ ID NO: 129)
KGEAGRP                (SEQ ID NO: 130)
GEAGRP                 (SEQ ID NO: 131)
EAGRPGRRGRPGLKGEQGEP   (SEQ ID NO: 132)
EAGRPGRRGRPGLKGEQGE    (SEQ ID NO: 133)
EAGRPGRRGRPGLKGEQG     (SEQ ID NO: 134)
EAGRPGRRGRPGLKGEQ      (SEQ ID NO: 135)
EAGRPGRRGRPGLKGE       (SEQ ID NO: 136)
EAGRPGRRGRPGLKG        (SEQ ID NO: 137)
EAGRPGRRGRPGLK         (SEQ ID NO: 138)
EAGRPGRRGRPGLK         (SEQ ID NO: 139)
EAGRPGRRGRPGL          (SEQ ID NO: 140)
EAGRPGRRGRPG           (SEQ ID NO: 141)
EAGRPGRRGRP            (SEQ ID NO: 142)
EAGRPGRRGR             (SEQ ID NO: 143)
EAGRPGRRG              (SEQ ID NO: 144)
EAGRPGRR               (SEQ ID NO: 145)
EAGRPGR                (SEQ ID NO: 146)
EAGRPG                 (SEQ ID NO: 147)
VTEDLCRAPDGKKGEAGRPG   (SEQ ID NO: 148)
TEDLCRAPDGKKGEAGRPGR   (SEQ ID NO: 149)
EDLCRAPDGKKGEAGRPGRR   (SEQ ID NO: 150)
DLCRAPDGKKGEAGRPGRRG   (SEQ ID NO: 151)
LCRAPDGKKGEAGRPGRRGR   (SEQ ID NO: 152)
CRAPDGKKGEAGRPGRRGRP   (SEQ ID NO: 153)
RAPDGKKGEAGRPGRRGRPG   (SEQ ID NO: 154)
APDGKKGEAGRPGRRGRPGL   (SEQ ID NO: 155)
PDGKKGEAGRPGRRGRPGLK   (SEQ ID NO: 156)
DGKKGEAGRPGRRGRPGLKG   (SEQ ID NO: 157)
GKKGEAGRPGRRGRPGLKGE   (SEQ ID NO: 158)
KKGEAGRPGRRGRPGLKGEQ   (SEQ ID NO: 159)
KGEAGRPGRRGRPGLKGEQG   (SEQ ID NO: 160)
GEAGRPGRRGRPGLKGEQGE   (SEQ ID NO: 161)
EDLCRAPDGKKGEAGRPG     (SEQ ID NO: 162)
DLCRAPDGKKGEAGRPGR     (SEQ ID NO: 163)
LCRAPDGKKGEAGRPGRR     (SEQ ID NO: 164)
CRAPDGKKGEAGRPGRRG     (SEQ ID NO: 165)
RAPDGKKGEAGRPGRRGR     (SEQ ID NO: 166)
APDGKKGEAGRPGRRGRP     (SEQ ID NO: 167)
PDGKKGEAGRPGRRGRPG     (SEQ ID NO: 168)
DGKKGEAGRPGRRGRPGL     (SEQ ID NO: 169)
GKKGEAGRPGRRGRPGLK     (SEQ ID NO: 170)
KKGEAGRPGRRGRPGLKG     (SEQ ID NO: 171)
KGEAGRPGRRGRPGLKGE     (SEQ ID NO: 172)
GEAGRPGRRGRPGLKGEQ     (SEQ ID NO: 173)
EAGRPGRRGRPGLKGEQG     (SEQ ID NO: 174)
DLCRAPDGKKGEAGRPG      (SEQ ID NO: 175)
LCRAPDGKKGEAGRPGR      (SEQ ID NO: 176)
CRAPDGKKGEAGRPGRR      (SEQ ID NO: 177)
RAPDGKKGEAGRPGRRG      (SEQ ID NO: 178)
APDGKKGEAGRPGRRGR      (SEQ ID NO: 179)
PDGKKGEAGRPGRRGRP      (SEQ ID NO: 180)
DGKKGEAGRPGRRGRPG      (SEQ ID NO: 181)
GKKGEAGRPGRRGRPGL      (SEQ ID NO: 182)
KKGEAGRPGRRGRPGLK      (SEQ ID NO: 183)
KGEAGRPGRRGRPGLKG      (SEQ ID NO: 184)
GEAGRPGRRGRPGLKGE      (SEQ ID NO: 185)
EAGRPGRRGRPGLKGEQ      (SEQ ID NO: 186)
LCRAPDGKKGEAGRPG       (SEQ ID NO: 187)
CRAPDGKKGEAGRPGR       (SEQ ID NO: 188)
RAPDGKKGEAGRPGRR       (SEQ ID NO: 189)
APDGKKGEAGRPGRRG       (SEQ ID NO: 190)
PDGKKGEAGRPGRRGR       (SEQ ID NO: 191)
DGKKGEAGRPGRRGRP       (SEQ ID NO: 192)
GKKGEAGRPGRRGRPG       (SEQ ID NO: 193)
KKGEAGRPGRRGRPGL       (SEQ ID NO: 194)
KGEAGRPGRRGRPGLK       (SEQ ID NO: 195)
GEAGRPGRRGRPGLKG       (SEQ ID NO: 196)
EAGRPGRRGRPGLKGE       (SEQ ID NO: 197)
CRAPDGKKGEAGRPG        (SEQ ID NO: 198)
RAPDGKKGEAGRPGR        (SEQ ID NO: 199)
APDGKKGEAGRPGRR        (SEQ ID NO: 200)
PDGKKGEAGRPGRRG        (SEQ ID NO: 201)
DGKKGEAGRPGRRGR        (SEQ ID NO: 202)
GKKGEAGRPGRRGRP        (SEQ ID NO: 203)
KKGEAGRPGRRGRPG        (SEQ ID NO: 204)
KGEAGRPGRRGRPGL        (SEQ ID NO: 205)
GEAGRPGRRGRPGLK        (SEQ ID NO: 206)
EAGRPGRRGRPGLKG        (SEQ ID NO: 207)
RAPDGKKGEAGRPG         (SEQ ID NO: 208)
APDGKKGEAGRPGR         (SEQ ID NO: 209)
PDGKKGEAGRPGRR         (SEQ ID NO: 210)
DGKKGEAGRPGRRG         (SEQ ID NO: 211)
GKKGEAGRPGRRGR         (SEQ ID NO: 212)
KKGEAGRPGRRGRP         (SEQ ID NO: 213)
KGEAGRPGRRGRPG         (SEQ ID NO: 214)
GEAGRPGRRGRPGL         (SEQ ID NO: 215)
EAGRPGRRGRPGLK         (SEQ ID NO: 216)
APDGKKGEAGRPG          (SEQ ID NO: 217)
PDGKKGEAGRPGR          (SEQ ID NO: 218)
DGKKGEAGRPGRR          (SEQ ID NO: 219)
GKKGEAGRPGRRG          (SEQ ID NO: 220)
KKGEAGRPGRRGR          (SEQ ID NO: 221)
KGEAGRPGRRGRP          (SEQ ID NO: 222)
GEAGRPGRRGRPG          (SEQ ID NO: 223)
EAGRPGRRGRPGL          (SEQ ID NO: 224)
PDGKKGEAGRPG           (SEQ ID NO: 225)
DGKKGEAGRPGR           (SEQ ID NO: 226)
GKKGEAGRPGRR           (SEQ ID NO: 227)
KKGEAGRPGRRG           (SEQ ID NO: 228)
KGEAGRPGRRGR           (SEQ ID NO: 229)
GEAGRPGRRGRP           (SEQ ID NO: 230)
EAGRPGRRGRPG           (SEQ ID NO: 231)
DGKKGEAGRPG            (SEQ ID NO: 232)
GKKGEAGRPGR            (SEQ ID NO: 233)
KKGEAGRPGRR            (SEQ ID NO: 234)
KGEAGRPGRRG            (SEQ ID NO: 235)
GEAGRPGRRGR            (SEQ ID NO: 236)
EAGRPGRRGRP            (SEQ ID NO: 237)
GKKGEAGRPG             (SEQ ID NO: 238)
KKGEAGRPGR             (SEQ ID NO: 239)
KGEAGRPGRR             (SEQ ID NO: 240)
GEAGRPGRRG             (SEQ ID NO: 241)
EAGRPGRRGR             (SEQ ID NO: 242)
KKGEAGRPG              (SEQ ID NO: 243)
KGEAGRPGR              (SEQ ID NO: 244)
GEAGRPGRR              (SEQ ID NO: 245)
EAGRPGRRG              (SEQ ID NO: 246)
KGEAGRPG               (SEQ ID NO: 247)
GEAGRPGR               (SEQ ID NO: 248)
EAGRPGRR               (SEQ ID NO: 249)
GEAGRPG                (SEQ ID NO: 250)
EAGRPGR                (SEQ ID NO: 251)
```

In an embodiment, the isolated peptide comprises EAGRP or EADSV, and has a sequence as set forth in any of the sequences above except for comprising one or more amino acid substitutions in the isolated peptide that are not in the EAGRP or EADSV portion thereof. The isolated peptide may have one of: 80% or greater identity with any one of SEQ ID NOS: 7-240, 85% or greater identity with any one of SEQ ID NOS: 7-240, 90% or greater identity with any one of SEQ ID NOS: 7-240, 95% or greater identity with any one of SEQ ID NOS: 7-240, or 99% identity with any one of SEQ ID NOS: 7-240. The isolated peptide comprising EAGRP or EADSV may have a sequence as set forth in SEQ ID NOS: 7-240 except for the substitutions therein outside the EAGRP or EADSV sequence, respectively. For example, the peptide is 20 amino acids long and comprises up to 10 amino acid substitutions outside of EAGRP or EADSV; for example, the peptide is 15 amino acids long and comprises up to 6, 7, 8, or 9 amino acid substitutions outside of EAGRP or EADSV (it is understood that these are non-limiting examples provided for the purpose of illustrating one aspect of the invention).

In a further non-limiting example, the isolated peptide comprising EAGRP or EADSV and having a sequence as set forth in SEQ ID NOS: 7-240 except for the substitutions therein outside the EAGRP or EADSV sequence, may comprise 1, 2, 3, 4, or 5 substitutions.

The substitution variants of the invention have at least one amino acid residue in the isolated peptide removed and a different residue inserted in its place. The sites of greatest interest for substitutional mutagenesis are outside the core sequences, i.e. in residues other than EADSV, EADSI, EAGRP, and EADYG. In an embodiment, one or more of the substitutions is a conservative substitution. Conservative substitutions are shown in Table 1 under the heading of "conservative substitutions." In an embodiment, one or more of the substitutions is a substitution as set forth in the third column of Table 1.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Modifications in the biological properties of the isolated peptide are accomplished by selecting substitutions that differ significantly in their effect on maintaining (a) the structure of the polypeptide backbone in the area of the substitution, (b) the charge or hydrophobicity of the molecule at the target site, or (c) the bulk of the side chain. Naturally occurring residues are divided into groups based on common side-chain properties:
(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

In an embodiment, the substitution variants of the invention comprise non-conservative substitutions. Non-conservative substitutions are made by exchanging a member of one of the classes (1) through (6) for another class.

In an embodiment, the substitution or substitutions improve solubility of the isolated peptide in the serum of a subject. In an embodiment, the substitution or substitutions improve the half-life of the isolated peptide in the body of a subject. An improvement is relative to the corresponding non-substituted peptide.

This invention also provides any of the above-described peptides with one substitution or with two substitutions in the sequence EADSV, EADSI, EAGRP, and EADYG, with the proviso that the peptide does not comprise the sequence DWEYS, DWDYS or EWDYG.

The isolated peptide can comprise both D-amino acids and L-amino acids. In an embodiment, all the amino acid residues of the peptide are D-amino acids. In an embodiment, all the amino acid residues of the peptide are L-amino acids.

A fusion protein is provided comprising the isolated peptide as described hereinabove, joined at an N-terminal amino acid or C-terminal amino acid thereof by a peptide bond to a second peptide or polypeptide or protein. In an embodiment, the fusion protein comprising the isolated peptide has a longer half-life in a human subject than the isolated peptide alone does. In an embodiment, the fusion protein comprising the isolated peptide is more soluble in the serum of a human subject than the isolated peptide alone is. In a preferred embodiment, the fusion protein is an isolated recombinant fusion protein created by recombinant DNA technology. In an embodiment, the peptide is fused to a functional domain of a second peptide or polypeptide or protein. In an embodiment, the peptide is fused to a functional domain of a second peptide which is a cell-penetrating peptide. In an embodiment, the cell-penetrating peptide is TAT, transportan or penetratin. In an embodiment, the peptide is fused to an immunoglobulin constant domain (Fc). In an embodiment, the peptide is fused to a human immunoglobulin constant domain.

Also provided is a composition comprising the isolated peptide as described hereinabove. Also provided is a composition comprising the fusion protein as described hereinabove.

A fusion protein is provided comprising an isolated peptide of 5 to 20 consecutive amino acid residues in length comprising the sequence $X_4WX_5YX_6$ (SEQ ID NO:6), wherein $X_4$ is D or E, wherein $X_5$ is D or E, and wherein $X_6$ is G or S, joined at an N or C terminal amino acid thereof by a peptide bond to a second peptide or polypeptide or protein. In a preferred embodiment, $X_4$ is D, $X_5$ is E, and $X_6$ is S. In an embodiment, $X_4$ is D, $X_5$ is D, and $X_6$ is S. In an embodiment, $X_4$ is E, $X_5$ is D, and $X_6$ is G. The second peptide or polypeptide or protein does not naturally occur immediately adjacent in sequence to the isolated peptide. In an embodiment, the second peptide or polypeptide or protein is from another species. In an embodiment, the second peptide or polypeptide or protein is recombinantly produced and not naturally produced. In a preferred embodiment, the second peptide or polypeptide or protein is not a toxin. In a preferred embodiment, the second peptide or polypeptide or protein is not a detectable marker. In an embodiment, the fusion protein comprising the isolated peptide has a longer half-life in a human subject than the isolated peptide alone does. In an embodiment, the fusion protein comprising the isolated peptide is more soluble in the serum of a human subject than the isolated peptide alone is. In a preferred embodiment, the fusion protein is an isolated recombinant fusion protein created by recombinant DNA technology. In an embodiment, the second peptide or polypeptide or protein is a functional domain of a polypeptide or protein. In an embodiment, the second peptide or polypeptide or protein is a cell-penetrating peptide. In an embodiment, the cell-penetrating peptide is TAT, transportan or penetratin. In an embodiment, the second peptide or polypeptide or protein is an immunoglobulin constant domain (Fc). In an embodiment, the immunoglobulin constant domain is human. In an embodiment, the immunoglobulin Fc domain is an IgG Fc domain. In an embodiment, the immunoglobulin Fc domain is an IgA Fc domain. In an embodiment, the immunoglobulin Fc domain is an IgM Fc domain. In an embodiment, the immunoglobulin Fc domain is a human immunoglobulin Fc domain. In an embodiment, the immunoglobulin Fc domain is an IgG1 Fc domain. A composition comprising the fusion protein and a carrier is also provided.

In an embodiment, isolated as used herein means non-naturally occurring.

A method of treating an autoimmune condition in a subject is provided comprising administering to the subject an isolated peptide, a fusion protein, or a composition, as described hereinabove, in an amount effective to treat an autoimmune condition in a subject.

In a most preferred embodiment, the autoimmune condition is systemic lupus erythematosus (SLE) or a complication thereof. In an embodiment, the condition is a renal pathology. In an embodiment, the condition is lupus nephritis. In an embodiment, the condition is neuropsychiatric SLE.

Also provided is a method of treating an autoimmune condition in a subject comprising administering to the subject an isolated peptide, a fusion protein, or a composition as described herein, in an amount effective to reduce circulating autoantibodies in a subject and thereby treat an autoimmune condition. In a preferred embodiment, the autoantibodies comprise an anti-double stranded DNA autoantibody. In a preferred embodiment, the autoantibodies comprise an anti-C1q autoantibody.

In one aspect, wherein the invention provides a method for treating an autoimmune condition in a subject, the autoimmune condition is systemic lupus erythematosus (SLE), neuropsychiatric SLE, acute disseminated encephalomyelitis (ADEM), alopecia areata, antiphospholipid syndrome, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Behçet's disease, celiac disease, Chagas disease, cold agglutinin disease, Crohn's disease, dermatomyositis, diabetes mellitus type 1, eosinophilic fascitis, gastrointestinal pemphigoid, Goodpasture's syndrome, Grave's syndrome, Guillain-Barré syndrome, Hashimoto's encephalopathy, Hashimoto's thyroiditis, lupus erythematosus, Miller-Fisher syndrome, mixed connective tissue disease, myasthenia gravis, pemphigus vulgaris, pernicious anaemia, polymyositis, psoriasis, psoriatic arthritis, relapsing polychondritis, rheumatoid arthritis, rheumatic fever, Sjögren's syndrome, temporal arteritis, transverse myelitis, ulcerative colitis, undifferentiated connective tissue disease, vasculitis, or Wegener's granulomatosis. In a preferred embodiment, the autoimmune condition is systemic SLE or neuropsychiatric SLE.

The invention encompasses compositions comprising the isolated peptides described herein or the fusion proteins described herein. In an embodiment, the composition is a pharmaceutical composition. In an embodiment the composition or pharmaceutical composition comprising one or more of the isolated peptides described herein or the fusion proteins described herein is substantially pure with regard to the isolated peptides described herein or the fusion proteins described herein. A composition or pharmaceutical composition comprising one or more of the isolated peptides described herein or the fusion proteins described herein is "substantially pure" with regard to that when at least 60% of a sample of the composition or pharmaceutical composition exhibits a single species of the isolated peptide or fusion protein. A substantially pure composition or pharmaceutical composition comprising one or more of the isolated peptides described herein or the fusion proteins described herein can comprise, in the portion thereof which is the isolated peptide or fusion protein, 60%, 70%, 80% or 90% of the isolated peptide or fusion protein of the single species, more usually about 95%, and preferably over 99%. Purity or homogeneity may tested by a number of means well known in the art, such as polyacrylamide gel electrophoresis or HPLC.

In an embodiment, the composition is a dimer or trimer of the isolated peptides. In an embodiment, the composition is a dimer or trimer of the fusion proteins.

Compositions or pharmaceutical compositions disclosed herein preferably comprise stabilizers to prevent loss of activity or structural integrity of the peptide or fusion protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH of 6.8 to 7.4.

In an embodiment the isolated peptides or fusion proteins disclosed herein are lyophilized and/or freeze dried and are reconstituted for use.

The invention encompasses compositions comprising the isolated peptides or fusion proteins described herein in a pharmaceutically acceptable carrier. As used herein, "pharmaceutically acceptable carrier" includes any material (including mixtures) which, when combined with an active ingredient, allows the ingredient to retain biological activity and is non-reactive with the subject's immune system. Examples include, but are not limited to, any of the standard pharmaceutical carriers such as one or more of phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000). In non-limiting examples, the can comprise one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxyethoxyl)ethoxy]ethyl (E)-octadec-9-enoate), disodium edetate dehydrate, sucrose, monobasic sodium phosphate monohydrate, and dibasic sodium phosphate dihydrate.

The compositions or pharmaceutical compositions described herein can also be lyophilized or provided in any suitable forms including, but not limited to, injectable solutions or inhalable solutions, gel forms and tablet forms.

The practice of the present invention can employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997).

In some embodiments, therapeutic administration of the isolated peptide, or of the composition comprising such, advantageously results in reduced incidence and/or amelioration of one or more symptoms of the autoimmune condition. In an embodiment, the said composition is a pharmaceutical composition. In some embodiments, therapeutic administration of the isolated fusion-protein or the composition comprising such advantageously results in reduced incidence and/or amelioration of one or more symptoms of the autoimmune condition. In an embodiment, the said composition is a pharmaceutical composition.

With respect to the therapeutic methods described herein, reference to compositions includes compositions comprising one or more additional agents. These compositions may further comprise suitable excipients, such as pharmaceutically acceptable excipients including buffers, which are well known in the art. The present invention can be used alone or in combination with other methods of treatment. In an embodiment, the other method of treatment comprise an immune-system modulating therapy.

The isolated peptides, fusion proteins, or compositions comprising such, can be administered to an subject via any suitable route. It should be apparent to a person skilled in the art that the examples described herein are not intended to be limiting but to be illustrative of the techniques available. Accordingly, in some embodiments, the they are administered to a subject in accord with known methods, such as intravenous administration, e.g., as a bolus or by continuous infusion over a period of time, by intramuscular, intraperitoneal, intracerebrospinal, transdermal, subcutaneous, intraarticular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution.

In some embodiments, the isolated peptide, fusion protein, or composition comprising such, is administered via site-specific or targeted local delivery techniques. Examples of site-specific or targeted local delivery techniques include various implantable depot sources or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of the isolated peptide or fusion protein of the invention may be used for administration. In some embodiments, the isolated peptide or fusion protein of the invention may be administered neat. In some embodiments, the isolated peptide or fusion protein of the invention and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular subject and that subject's medical history.

Therapeutic formulations of the peptide or fusion protein used in accordance with the present invention are prepared for storage by mixing with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the peptide or fusion protein are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the isolated peptide or fusion protein, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for in vivo administration must be sterile. This is readily accomplished by, for example, filtration through sterile filtration membranes.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Emulsion compositions of the invention can be those prepared by mixing an isolated peptide or fusion protein of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The term "subject" is intended to include mammals, e.g., humans, dogs, cows, horses, pigs, sheep, goats, cats, mice, rabbits, rats, and also includes avians. In specific embodiments of the invention, the subject is a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

Antibody to C1q has been implicated in lupus nephritis, and is found in 30 to 50% of lupus patients [14]. Indeed, antibody to C1q correlates more strongly with renal disease than antibody to dsDNA and increased serum levels of anti-C1q antibodies correlate with flares [15]. Since C1q together with natural IgM autoantibodies plays a major role in maintenance of self-tolerance through opsonization of apoptotic material, it has been postulated that anti-C1q antibodies might decrease the availability of C1q for this tolerogenic function. Anti-C1q antibodies may also contribute to lupus pathogenesis by binding to IC in target organs. In support of this model are data that monoclonal anti-C1q antibodies administered to mice exacerbate glomerular immunoglobulin deposition by anti-glomerular basement membrane antibodies [16], although they do not induce disease by themselves.

This laboratory has previously generated a murine monoclonal antibody R4A which binds to dsDNA [17]. By screening a peptide library, it was shown that R4A binds a consensus sequence D/EWD/EYS/G Immunization of BALB/c mice with a multimeric configuration of the DWEYS peptide induces the formation of antibodies that cross-react with dsDNA, deposit in glomeruli and induce proteinuria [18]. The consensus sequence is present in the extracellular region of the N-methyl-D-aspartate receptor (NMDAR) in both mice and humans. In mice, antibodies to dsDNA and DWEYS bind neuronal NMDAR, induce apoptosis and can cause some neuropsychiatric manifestations of lupus if they gain access to brain tissue [19]. Antibodies cross-reactive with both dsDNA and DWEYS peptide are present in approximately 40% of lupus patients. [19]

Material and Methods

Mice—Female C1q-/- C57BL/6J mice were obtained from Dr. Keith Elkon, University of Washington and female C57BL/6J from Jackson Laboratories (Bar Harbor, Me., USA). Mice were 8-16 weeks of age.

ELISAs—Costar half-volume 96-well plates (Corning, N.Y.) were used for C1q ELISAs and Immulon 2HB 96-well plates (Milford, Mass.) were used for DNA ELISAs. C1q was purchased from Comptech (Tyler, Tex.) and adsorbed to 96-well plate (50 µg/ml) Plates were blocked with 2% BSA in PBS for 1 hour at RT. R4A antibody or IgG2b control immunoglobulin (MPC-11 hybridoma, ATCC, Manassas, Va.) was added for 1 hour at RT at various concentrations of NaCl. Cytokine ELISA was performed according to manufacturer's protocol (BD Biosciences, San Diego, Calif.). C1q collagen-tail of C1q was prepared as described in [21]. Reagents used in vivo experiments were tested for LPS content by LAL assay and were found to have less than 0.05 EU/ml.

Glomerular binding assay—Glomeruli were isolated from C1q-/- or wild type C57/BL6J mice [22]. Ten to 20 glomeruli were attached per slide and acetone fixed. Some slides were treated with DNAse (Sigma) at 100 µg/ml in 5 mM CaCl and 0.9% NaCl for 45 min at 37° C. or with PBS alone. After blocking with 10% goat serum, primary antibodies were added. Secondary antibodies were added at a 1:200 dilution for FITC-labeled anti-mouse IgG (BD) or a 1:10 dilution for FITC-labeled anti-human IgG (Inova diagnostics).

Isolation of human anti-DWEYS antibodies—Lupus sera known to have antibodies reactive to DWEYS peptide were incubated with a sepharose 4B resin coupled to DWEYS peptide (AnaSpec Inc. San Jose, Calif.) for 12 hours at 4° C. The resin was washed with PBS prior to elution of bound antibodies with a 0.2 M glycine buffer pH 3.

Generation of human monoclonal antibody—The monoclonal H6 antibody was obtained as described [23].

In vivo administration of R4A or IgG2b—Antibodies were labeled with infrared (IR) according to manufacturer (Li-corbiosciences, Lincoln, Nebr.) and were injected intravenously at 200 µg/mouse. Mice were euthanized 4 hours after injection, the kidneys were perfused with saline in order to remove intra-vascular blood and the whole kidney was analyzed in an Odyssey Clx imaging system. A lysate was also prepared from the kidneys and an aliquot measured for IR signal.

Results

R4A was also found to bind the decapeptide WCEADYGRCP (SEQ ID NO:252) in the peptide library. Because R4A bound the consensus pentapeptide D/EWD/EYS/G, (SEQ ID NO:6) it was hypothesized to bind the EADYG sequence (SEQ ID NO:4), which shares 4 of 5 amino acids with the consensus sequence [20]. A peptide blast query using the EADYG peptide sequence (SEQ ID NO:4) through the National Center for Biotechnology information (NLM-NIH) search engine, identified a homologous sequence present in C1q globular domain (GSEADSV) (NP 001002259.1, NCBI, NLM, NIH) (SEQ ID NO:30). Herein it is demonstrated for the first time that antibodies to dsDNA cross-react with C1q and play a potential role in the pathogenesis of lupus through deposition in glomeruli.

Figures 1E, 1F, 1G:
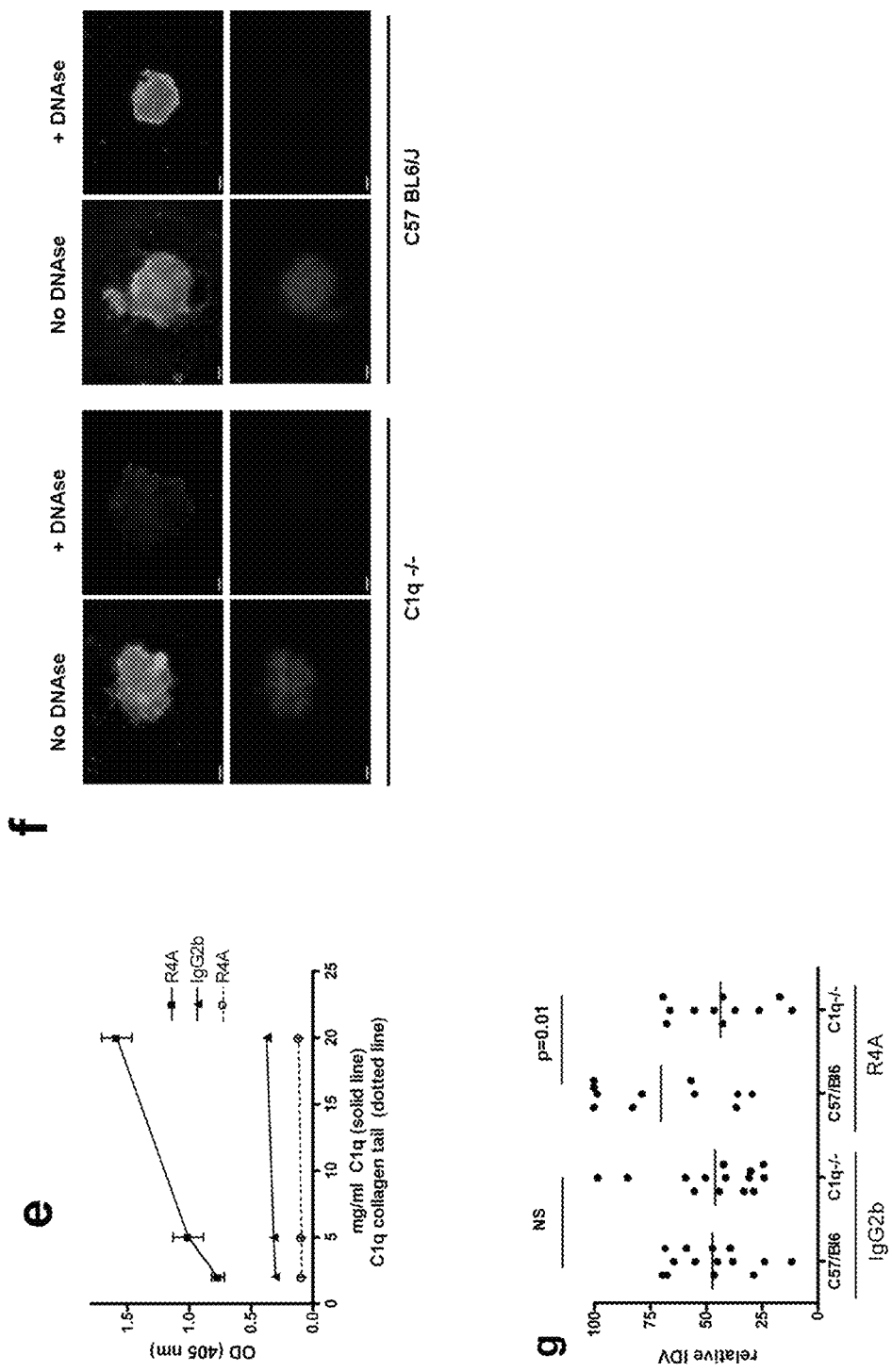

R4A antibody binds to human complement C1q: The anti-dsDNA antibody R4A bound to the EADYG peptide and to C1q in a dose-dependent manner (FIGS. 1A and 1B). In addition, both peptides EADYG and DWEYS inhibited R4A binding to C1q (FIG. 1C) and C1q inhibited R4A binding to dsDNA (FIG. 1D). These results demonstrate R4A reactivity to dsDNA, C1q and derived peptides. The GSEADSV sequence of C1q is in the globular head. In an attempt to verify that R4A binds this epitope, binding experiments were performed with purified collagen tail of C1q. R4A did not bind C1q collagen tail suggesting that the binding site is present in the globular region of C1q (FIG. 1E).

It was next tested whether R4A bound isolated glomeruli from wild type and C1q-/- C57 BL6/J mice. R4A antibody strongly stained glomeruli from wild type mice both before and after DNAse treatment (FIG. 1F). In contrast, R4A bound glomeruli from C1q-/- mice prior to DNAse treatment but not after DNAse treatment. Moreover, C1q-/- mice injected intravenously with R4A had significantly lower levels of antibody deposition in their kidney than wild type mice while an isotype control antibody deposited equally in kidney of both strains (FIG. 1G).

Figures 2A, 2B, 2C:
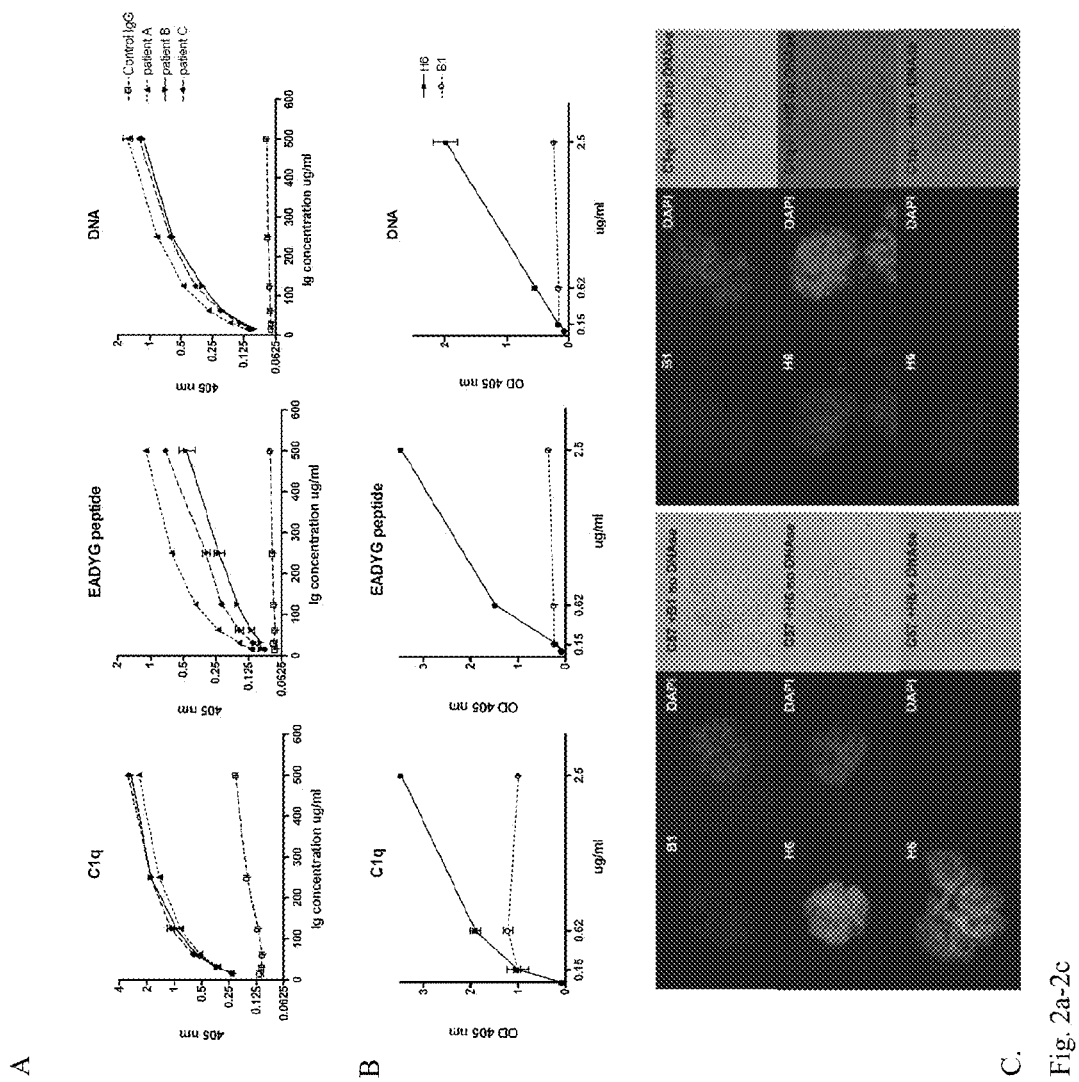
FIG. 2A-2C. Human anti-DWEYS antibodies bind C1q. 2A. Polyclonal affinity purified DWEYS binding antibodies bind human C1q, EADYG peptide and dsDNA. Purified human IgG was used as control. 2B. Human monoclonal antibody binds C1q. A monoclonal anti-DWEYS antibody, H6, derived from a lupus patient binds native human C1q, EADYG peptide and dsDNA. B1 is a control human antibody. 2C. H6 binding to glomeruli. Glomeruli from wild type or C1q−/− mice were incubated with antibodies H6 or B1. DAPI was used to visualize DNA.

Anti-DWEYS antibody enriched from lupus patients binds to C1q: To understand whether antibodies from serum of lupus patients shared cross-reactivity to C1q, we affinity purified DWEYS-reactive antibodies from serum of three lupus patients. All preparations bound C1q, EADYG peptide and dsDNA (FIG. 2A). Purified human IgG did not bind any of the 3 antigens.

A monoclonal antibody obtained from lupus patients binds DNA, C1q and EADYG peptide and binds glomeruli ex vivo. H6, a human monoclonal antibody isolated from a peripheral blood B cell of a lupus patient, previously shown to bind to dsDNA and DWEYS peptide was demonstrated by ELISA to bind both C1q and EADYG (FIG. 2B) [23, 24]. Moreover, like R4A, H6 bound glomeruli from wild type mice before and after DNAse treatment but bound glomeruli from C1q-/- mice prior to, but not after, DNAse treatment (FIG. 2C). B1, a human monoclonal antibody with no reactivity to DNA or DWEYS, failed to bind glomeruli from either mouse strain.

Discussion

In this study it is demonstrated for the first time that a subset of anti-DNA antibodies cross-reacts with C1q as well as NMDAR. The finding of anti-C1q antibodies in lupus, especially in patients with nephritis, is known, however the presence of anti-DNA antibodies cross-reactive with C1q is novel. It is demonstrated that R4A binding to C1q could be inhibited by both the DWEYS and EADYG peptides. It is also important to note that R4A binding to C1q is not limited to solid phase; it was possible to show that R4A binds fluid phase C1q through inhibition of binding to immobilized dsDNA. The binding site of R4A in C1q is in the globular region since it did not bind isolated collagen tail.

Lupus nephritis can be initiated by the deposition of anti-dsDNA antibody in glomeruli. R4A has been shown to bind glomeruli even after removal of exposed DNA binding sites through DNAse treatment. It was considered, therefore, that R4A might bind C1q present in glomeruli. The study of antibody binding to isolated glomeruli has been used as a surrogate model for anti-DNA antibody binding in vivo and may identify nephritogenic potential of these antibodies. The results demonstrate that C1q is a major target antigen in wild type glomeruli. These results are in agreement with data obtained from in vivo experiments of R4A binding to kidney after intravenous administration of the antibody.

In an attempt to investigate whether a similar phenomenon of cross-reactivity could be found in patients with lupus, it is demonstrated that a subset of isolated anti-DNA antibodies from lupus patients also showed cross-reactivity to C1q and EADYG peptide [1, 2]. The normal plasma concentrations of C1q range between 100 and 200 µg/ml; thus, the concentration of C1q in plasma is sufficient for in vivo antibody binding [25].

Since this laboratory has previously shown that antibodies with this cross-reactivity are present in 30 to 40% of SLE patients, and only rarely in patients lacking detectable DNA reactivity, it is believed these antibodies are frequent in SLE patients. In addition, a human monoclonal antibody to DNA was also found to bind to isolated glomeruli and C1q was a major target antigen as well, similarly to what we observed for R4A.

This cross-reactivity appears crucial in the binding of this subset of anti-DNA antibodies to glomeruli. This observation helps explain the multiple studies showing that anti-C1q antibodies are present in approximately 50% of lupus patients, almost exclusively in patients who also harbor anti-dsDNA antibodies, and are highly predictive of renal disease. The data demonstrate that anti-C1q antibodies could contribute to IC-mediated glomerulonephritis by enhancing IC deposition in glomeruli.

There are a number of studies that show the critical contribution of DCs to systemic inflammation in SLE and to glomerulonephritis [26]. R4A-like antibodies may also bind and remove soluble C1q, thereby causing a functional deficiency of C1q and enhanced systemic inflammation.

Overall, these studies demonstrate a novel cross-reactivity between DNA and C1q and provide evidence supporting a role for cross-reactive antibodies in SLE.

REFERENCES

[1] Paul E, Manheimer-Lory A, Livneh A, Solomon A, Aranow C, Ghossein C et al. Pathogenic anti-DNA antibodies in SLE: idiotypic families and genetic origins. IntRevImmunol, 1990; 5:295-313.

[2] Sasaki T, Hatakeyama A, Shibata S, Osaki H, Suzuki M, Horie K et al. Heterogeneity of immune complex-derived anti-DNA antibodies associated with lupus nephritis. Kidney Int, 1991; 39:746-53.

[3] Bruijn J. Fundamentals of Renal Pathology. Springer New York, N.Y.; 2007. [4] Finke D, Eloranta M L, Ronnblom L. Endogenous type I interferon inducers in autoimmune diseases. Autoimmunity, 2009; 42:349-52.

[5] Yasuda K, Richez C, Uccellini M B, Richards R J, Bonegio R G, Akira S et al. Requirement for DNA CpG content in TLR9-dependent dendritic cell activation induced by DNA-containing immune complexes. J Immunol, 2009; 183:3109-17.

[6] Kishore U, Reid K B. C1q: structure, function, and receptors Immunopharmacology, 2000; 49:159-70.

[7] van K C, Fiore N, Trouw L A, Csomor E, Xu W, Castellano G et al. Complement production and regulation by dendritic cells: molecular switches between tolerance and immunity. MolImmunol, 2008; 45:4064-72.

[8] Csomor E, Bajtay Z, Sandor N, Kristof K, Arlaud G J, Thiel S et al. Complement protein C1q induces maturation of human dendritic cells. MolImmunol, 2007; 44:3389-97.

[9] Liu S, Wu J, Zhang T, Qian B, Wu P, Li L et al. Complement C1q chemoattracts human dendritic cells and enhances migration of mature dendritic cells to CCL19 via activation of AKT and MAPK pathways. MolImmunol, 2008.

[10] Manderson A P, Botto M, Walport M J. The role of complement in the development of systemic lupus erythematosus. AnnuRevImmunol, 2004; 22:431-56.

[11] Nicholson-Weller A, Klickstein L B. C1q-binding proteins and C1q receptors. CurrOpinImmunol, 1999; 11:42-6.

[12] Santer D M, Hall B E, George T C, Tangsombatvisit S, Liu C L, Arkwright P D et al. C1q deficiency leads to the defective suppression of IFN-alpha in response to nucleoprotein containing immune complexes. J Immunol, 2010; 185:4738-49.

[13] Lood C, Gullstrand B, Truedsson L, Olin A I, Alm G V, Ronnblom L et al. C1q inhibits immune complex-induced interferon-alpha production in plasmacytoid dendritic cells: a novel link between C1q deficiency and systemic lupus erythematosus pathogenesis. Arthritis Rheum, 2009; 60:3081-90.

[14] Trouw L A, Daha M R. Role of anti-C1q autoantibodies in the pathogenesis of lupus nephritis. ExpertOpinBiolTher, 2005; 5:243-51.

[15] Marto N, Bertolaccini M L, Calabuig E, Hughes G R, Khamashta M A. Anti-C1q antibodies in nephritis: correlation between titres and renal disease activity and positive predictive value in systemic lupus erythematosus. AnnRheumDis, 2005; 64:444-8.

[16] Trouw L A, Groeneveld T W, Seelen M A, Duijs J M, Bajema I M, Prins F A et al. Anti-C1q autoantibodies deposit in glomeruli but are only pathogenic in combination with glomerular C1q-containing immune complexes. JClinInvest, 2004; 114:679-88.

[17] Shefner R, Kleiner G, Turken A, Papazian L, Diamond B. A novel class of anti-DNA antibodies identified in BALB/c mice. JExpMed, 1991; 173:287-96. [18] Putterman C, Diamond B Immunization with a peptide surrogate for doublestranded DNA (dsDNA) induces autoantibody production and renal immunoglobulin deposition. JExpMed, 1998; 188:29-38.

[19] Kowal C, Degiorgio L A, Lee J Y, Edgar M A, Huerta P T, Volpe B T et al. Human lupus autoantibodies against NMDA receptors mediate cognitive impairment. ProcNatlAcadSciUSA, 2006; 103:19854-9.

[20] Gaynor B, Putterman C, Valadon P, Spatz L, Scharff M D, Diamond B. Peptide inhibition of glomerular deposition of an anti-DNA antibody. ProcNatlAcadSciUSA, 1997; 94:1955-60.

[21] Reid K B. Isolation, by partial pepsin digestion, of the three collagen-like regions present in subcomponent C1q of the first component of human complement. Biochem J, 1976; 155:5-17.

[22] Budhai L, Oh K, Davidson A. An in vitro assay for detection of glomerular binding IgG autoantibodies in patients with systemic lupus erythematosus. JClinInvest, 1996; 98:1585-93.

[23] Zhang J, Jacobi A M, Mackay M, Aranow C, Wang T, Chinnasamy P et al. Identification of DNA-reactive B cells in patients with systemic lupus erythematosus JImmunolMethods, 2008; 338:79-84.

[24] Zhang J, Jacobi A M, Wang T, Diamond B. Pathogenic autoantibodies in systemic lupus erythematosus are derived from both self-reactive and non-self-reactive B cells. MolMed, 2008; 14:675-81.

[25] Sontheimer R D, Racila E, Racila D M. C1q: its functions within the innate and adaptive immune responses and its role in lupus autoimmunity. JInvest Dermatol, 2005; 125:14-23.

[26] Castellano G, Trouw L A, Fiore N, Daha M R, Schena F P, van Kooten C. Infiltrating dendritic cells contribute to local synthesis of C1q in murine and human lupus nephritis. Mol Immunol, 2010; 47:2129-37.

What is claimed is:

1. A fusion protein comprising an isolated peptide of 5 to 20 consecutive amino acid residues in length comprising the sequence EADYG (SEQ ID NO:4) joined at an N-terminal amino acid or C-terminal amino acid thereof by a peptide bond to a second peptide or a polypeptide or a protein, which does not comprise WCEADYGRCP (SEQ ID NO:252).

2. The fusion protein of claim 1, wherein all the amino acid residues of the isolated peptide are D-amino acids.

3. The fusion protein of any of claim 1, wherein all the amino acid residues of the isolated peptide are L-amino acids.

SEQUENCE LISTING

<160> NUMBER OF SEQ ID NOS: 252

<210> SEQ ID NO 1
<211> LENGTH: 5
<212> TYPE: PRT
<213> ORGANISM: Artificial Sequence
<220> FEATURE:
<223> OTHER INFORMATION: fusion protein
<220> FEATURE:
<221> NAME/KEY: misc_feature
<222> LOCATION: (3)..(3)
<223> OTHER INFORMATION: x = D or G
<220> FEATURE:
<221> NAME/KEY: misc_feature
<222> LOCATION: (4)..(4)
<223> OTHER INFORMATION: x = S or R
<220> FEATURE:
<221> NAME/KEY: misc_feature
<222> LOCATION: (5)..(5)
<223> OTHER INFORMATION: x = V or P or I or G

<400> SEQUENCE: 1

Glu Ala Xaa Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: fusion protein

<400> SEQUENCE: 2

Glu Ala Asp Ser Val
1               5

<210> SEQ ID NO 3
<211> LENGTH: 5
<212> TYPE: PRT
<213> ORGANISM: Artificial Sequence
<220> FEATURE:
<223> OTHER INFORMATION: fusion protein

<400> SEQUENCE: 3

Glu Ala Gly Arg Pro
1               5

<210> SEQ ID NO 4
<211> LENGTH: 5
<212> TYPE: PRT
<213> ORGANISM: Artificial Sequence
<220> FEATURE:
<223> OTHER INFORMATION: fusion protein

<400> SEQUENCE: 4

Glu Ala Asp Tyr Gly
1               5

<210> SEQ ID NO 5
<211> LENGTH: 5
<212> TYPE: PRT
<213> ORGANISM: Artificial Sequence
<220> FEATURE:
<223> OTHER INFORMATION: fusion protein

<400> SEQUENCE: 5

Glu Ala Asp Ser Ile
1               5

```
<210> SEQ ID NO 6
<211> LENGTH: 5
<212> TYPE: PRT
<213> ORGANISM: Artificial Sequence
<220> FEATURE:
<223> OTHER INFORMATION: fusion protein
<220> FEATURE:
<221> NAME/KEY: MISC_FEATURE
<222> LOCATION: (1)..(1)
<223> OTHER INFORMATION: x = D or E
<220> FEATURE:
<221> NAME/KEY: MISC_FEATURE
<222> LOCATION: (3)..(3)
<223> OTHER INFORMATION: x = D or E
<220> FEATURE:
<221> NAME/KEY: MISC_FEATURE
<222> LOCATION: (5)..(5)
<223> OTHER INFORMATION: x = G or S

<400> SEQUENCE: 6

Xaa Trp Xaa Tyr Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: fusion protein

<400> SEQUENCE: 7

Glu Ala Asp Ser Val Phe
1               5

<210> SEQ ID NO 8
<211> LENGTH: 7
<212> TYPE: PRT
<213> ORGANISM: Artificial Sequence
<220> FEATURE:
<223> OTHER INFORMATION: fusion protein

<400> SEQUENCE: 8

Glu Ala Asp Ser Val Phe Ser
1               5

<210> SEQ ID NO 9
<211> LENGTH: 8
<212> TYPE: PRT
<213> ORGANISM: Artificial Sequence
<220> FEATURE:
<223> OTHER INFORMATION: fusion protein

<400> SEQUENCE: 9

Glu Ala Asp Ser Val Phe Ser Gly
1               5

<210> SEQ ID NO 10
<211> LENGTH: 9
<212> TYPE: PRT
<213> ORGANISM: Artificial Sequence
<220> FEATURE:
<223> OTHER INFORMATION: fusion protein

<400> SEQUENCE: 10

Glu Ala Asp Ser Val Phe Ser Gly Phe
1               5

<210> SEQ ID NO 11
```

```
<211> LENGTH: 10
<212> TYPE: PRT
<213> ORGANISM: Artificial Sequence
<220> FEATURE:
<223> OTHER INFORMATION: fusion protein

<400> SEQUENCE: 11

Glu Ala Asp Ser Val Phe Ser Gly Phe Leu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: fusion protein

<400> SEQUENCE: 12

Glu Ala Asp Ser Val Phe Ser Gly Phe Leu Ile
1               5                   10

<210> SEQ ID NO 13
<211> LENGTH: 12
<212> TYPE: PRT
<213> ORGANISM: Artificial Sequence
<220> FEATURE:
<223> OTHER INFORMATION: fusion protein

<400> SEQUENCE: 13

Glu Ala Asp Ser Val Phe Ser Gly Phe Leu Ile Phe
1               5                   10

<210> SEQ ID NO 14
<211> LENGTH: 13
<212> TYPE: PRT
<213> ORGANISM: Artificial Sequence
<220> FEATURE:
<223> OTHER INFORMATION: fusion protein

<400> SEQUENCE: 14

Glu Ala Asp Ser Val Phe Ser Gly Phe Leu Ile Phe Pro
1               5                   10

<210> SEQ ID NO 15
<211> LENGTH: 14
<212> TYPE: PRT
<213> ORGANISM: Artificial Sequence
<220> FEATURE:
<223> OTHER INFORMATION: fusion protein

<400> SEQUENCE: 15

Glu Ala Asp Ser Val Phe Ser Gly Phe Leu Ile Phe Pro Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: fusion protein

<400> SEQUENCE: 16

Glu Ala Asp Ser Val Phe Ser Gly Phe Leu Ile Phe Pro Ser Ala
1               5                   10                  15

<210> SEQ ID NO 17
<211> LENGTH: 20
```

<212> TYPE: PRT
<213> ORGANISM: Artificial Sequence
<220> FEATURE:
<223> OTHER INFORMATION: fusion protein

<400> SEQUENCE: 17

Trp Val Glu Lys Asp Pro Lys Lys Gly His Ile Tyr Gln Gly Ser Glu
1               5                   10                  15

Ala Asp Ser Val
            20

<210> SEQ ID NO 18
<211> LENGTH: 19
<212> TYPE: PRT
<213> ORGANISM: Artificial Sequence
<220> FEATURE:
<223> OTHER INFORMATION: fusion protein

<400> SEQUENCE: 18

Val Glu Lys Asp Pro Lys Lys Gly His Ile Tyr Gln Gly Ser Glu Ala
1               5                   10                  15

Asp Ser Val

<210> SEQ ID NO 19
<211> LENGTH: 18
<212> TYPE: PRT
<213> ORGANISM: Artificial Sequence
<220> FEATURE:
<223> OTHER INFORMATION: fusion protein

<400> SEQUENCE: 19

Glu Lys Asp Pro Lys Lys Gly His Ile Tyr Gln Gly Ser Glu Ala Asp
1               5                   10                  15

Ser Val

<210> SEQ ID NO 20
<211> LENGTH: 17
<212> TYPE: PRT
<213> ORGANISM: Artificial Sequence
<220> FEATURE:
<223> OTHER INFORMATION: fusion protein

<400> SEQUENCE: 20

Lys Asp Pro Lys Lys Gly His Ile Tyr Gln Gly Ser Glu Ala Asp Ser
1               5                   10                  15

Val

<210> SEQ ID NO 21
<211> LENGTH: 16
<212> TYPE: PRT
<213> ORGANISM: Artificial Sequence
<220> FEATURE:
<223> OTHER INFORMATION: fusion protein

<400> SEQUENCE: 21

Asp Pro Lys Lys Gly His Ile Tyr Gln Gly Ser Glu Ala Asp Ser Val
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: fusion protein

```
<400> SEQUENCE: 22

Pro Lys Lys Gly His Ile Tyr Gln Gly Ser Glu Ala Asp Ser Val
1               5                   10                  15

<210> SEQ ID NO 23
<211> LENGTH: 14
<212> TYPE: PRT
<213> ORGANISM: Artificial Sequence
<220> FEATURE:
<223> OTHER INFORMATION: fusion protein

<400> SEQUENCE: 23

Lys Lys Gly His Ile Tyr Gln Gly Ser Glu Ala Asp Ser Val
1               5                   10

<210> SEQ ID NO 24
<211> LENGTH: 13
<212> TYPE: PRT
<213> ORGANISM: Artificial Sequence
<220> FEATURE:
<223> OTHER INFORMATION: fusion protein

<400> SEQUENCE: 24

Lys Gly His Ile Tyr Gln Gly Ser Glu Ala Asp Ser Val
1               5                   10

<210> SEQ ID NO 25
<211> LENGTH: 12
<212> TYPE: PRT
<213> ORGANISM: Artificial Sequence
<220> FEATURE:
<223> OTHER INFORMATION: fusion protein

<400> SEQUENCE: 25

Gly His Ile Tyr Gln Gly Ser Glu Ala Asp Ser Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: fusion protein

<400> SEQUENCE: 26

His Ile Tyr Gln Gly Ser Glu Ala Asp Ser Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: fusion protein

<400> SEQUENCE: 27

Ile Tyr Gln Gly Ser Glu Ala Asp Ser Val
1               5                   10

<210> SEQ ID NO 28
<211> LENGTH: 9
<212> TYPE: PRT
<213> ORGANISM: Artificial Sequence
<220> FEATURE:
<223> OTHER INFORMATION: fusion protein

<400> SEQUENCE: 28
```

Tyr Gln Gly Ser Glu Ala Asp Ser Val
1               5

<210> SEQ ID NO 29
<211> LENGTH: 8
<212> TYPE: PRT
<213> ORGANISM: Artificial Sequence
<220> FEATURE:
<223> OTHER INFORMATION: fusion protein

<400> SEQUENCE: 29

Gln Gly Ser Glu Ala Asp Ser Val
1               5

<210> SEQ ID NO 30
<211> LENGTH: 7
<212> TYPE: PRT
<213> ORGANISM: Artificial Sequence
<220> FEATURE:
<223> OTHER INFORMATION: fusion protein

<400> SEQUENCE: 30

Gly Ser Glu Ala Asp Ser Val
1               5

<210> SEQ ID NO 31
<211> LENGTH: 6
<212> TYPE: PRT
<213> ORGANISM: Artificial Sequence
<220> FEATURE:
<223> OTHER INFORMATION: fusion protein

<400> SEQUENCE: 31

Ser Glu Ala Asp Ser Val
1               5

<210> SEQ ID NO 32
<211> LENGTH: 20
<212> TYPE: PRT
<213> ORGANISM: Artificial Sequence
<220> FEATURE:
<223> OTHER INFORMATION: fusion protein

<400> SEQUENCE: 32

Val Glu Lys Asp Pro Lys Lys Gly His Ile Tyr Gln Gly Ser Glu Ala
1               5                   10                  15

Asp Ser Val Phe
            20

<210> SEQ ID NO 33
<211> LENGTH: 20
<212> TYPE: PRT
<213> ORGANISM: Artificial Sequence
<220> FEATURE:
<223> OTHER INFORMATION: fusion protein

<400> SEQUENCE: 33

Glu Lys Asp Pro Lys Lys Gly His Ile Tyr Gln Gly Ser Glu Ala Asp
1               5                   10                  15

Ser Val Phe Ser
            20

<210> SEQ ID NO 34
<211> LENGTH: 20
<212> TYPE: PRT

<213> ORGANISM: Artificial Sequence
<220> FEATURE:
<223> OTHER INFORMATION: fusion protein

<400> SEQUENCE: 34

Lys Asp Pro Lys Lys Gly His Ile Tyr Gln Gly Ser Glu Ala Asp Ser
1               5                   10                  15

Val Phe Ser Gly
            20

<210> SEQ ID NO 35
<211> LENGTH: 20
<212> TYPE: PRT
<213> ORGANISM: Artificial Sequence
<220> FEATURE:
<223> OTHER INFORMATION: fusion protein

<400> SEQUENCE: 35

Asp Pro Lys Lys Gly His Ile Tyr Gln Gly Ser Glu Ala Asp Ser Val
1               5                   10                  15

Phe Ser Gly Phe
            20

<210> SEQ ID NO 36
<211> LENGTH: 20
<212> TYPE: PRT
<213> ORGANISM: Artificial Sequence
<220> FEATURE:
<223> OTHER INFORMATION: fusion protein

<400> SEQUENCE: 36

Pro Lys Lys Gly His Ile Tyr Gln Gly Ser Glu Ala Asp Ser Val Phe
1               5                   10                  15

Ser Gly Phe Leu
            20

<210> SEQ ID NO 37
<211> LENGTH: 20
<212> TYPE: PRT
<213> ORGANISM: Artificial Sequence
<220> FEATURE:
<223> OTHER INFORMATION: fusion protein

<400> SEQUENCE: 37

Lys Lys Gly His Ile Tyr Gln Gly Ser Glu Ala Asp Ser Val Phe Ser
1               5                   10                  15

Gly Phe Leu Ile
            20

<210> SEQ ID NO 38
<211> LENGTH: 20
<212> TYPE: PRT
<213> ORGANISM: Artificial Sequence
<220> FEATURE:
<223> OTHER INFORMATION: fusion protein

<400> SEQUENCE: 38

Lys Gly His Ile Tyr Gln Gly Ser Glu Ala Asp Ser Val Phe Ser Gly
1               5                   10                  15

Phe Leu Ile Phe
            20

<210> SEQ ID NO 39
<211> LENGTH: 20

<212> TYPE: PRT
<213> ORGANISM: Artificial Sequence
<220> FEATURE:
<223> OTHER INFORMATION: fusion protein

<400> SEQUENCE: 39

Gly His Ile Tyr Gln Gly Ser Glu Ala Asp Ser Val Phe Ser Gly Phe
1               5                   10                  15

Leu Ile Phe Pro
            20

<210> SEQ ID NO 40
<211> LENGTH: 20
<212> TYPE: PRT
<213> ORGANISM: Artificial Sequence
<220> FEATURE:
<223> OTHER INFORMATION: fusion protein

<400> SEQUENCE: 40

His Ile Tyr Gln Gly Ser Glu Ala Asp Ser Val Phe Ser Gly Phe Leu
1               5                   10                  15

Ile Phe Pro Ser
            20

<210> SEQ ID NO 41
<211> LENGTH: 20
<212> TYPE: PRT
<213> ORGANISM: Artificial Sequence
<220> FEATURE:
<223> OTHER INFORMATION: fusion protein

<400> SEQUENCE: 41

Ile Tyr Gln Gly Ser Glu Ala Asp Ser Val Phe Ser Gly Phe Leu Ile
1               5                   10                  15

Phe Pro Ser Ala
            20

<210> SEQ ID NO 42
<211> LENGTH: 19
<212> TYPE: PRT
<213> ORGANISM: Artificial Sequence
<220> FEATURE:
<223> OTHER INFORMATION: fusion protein

<400> SEQUENCE: 42

Glu Lys Asp Pro Lys Lys Gly His Ile Tyr Gln Gly Ser Glu Ala Asp
1               5                   10                  15

Ser Val Phe

<210> SEQ ID NO 43
<211> LENGTH: 19
<212> TYPE: PRT
<213> ORGANISM: Artificial Sequence
<220> FEATURE:
<223> OTHER INFORMATION: fusion protein

<400> SEQUENCE: 43

Lys Asp Pro Lys Lys Gly His Ile Tyr Gln Gly Ser Glu Ala Asp Ser
1               5                   10                  15

Val Phe Ser

<210> SEQ ID NO 44
<211> LENGTH: 19
<212> TYPE: PRT

```
<213> ORGANISM: Artificial Sequence
<220> FEATURE:
<223> OTHER INFORMATION: fusion protein

<400> SEQUENCE: 44

Asp Pro Lys Lys Gly His Ile Tyr Gln Gly Ser Glu Ala Asp Ser Val
1               5                   10                  15

Phe Ser Gly

<210> SEQ ID NO 45
<211> LENGTH: 19
<212> TYPE: PRT
<213> ORGANISM: Artificial Sequence
<220> FEATURE:
<223> OTHER INFORMATION: fusion protein

<400> SEQUENCE: 45

Pro Lys Lys Gly His Ile Tyr Gln Gly Ser Glu Ala Asp Ser Val Phe
1               5                   10                  15

Ser Gly Phe

<210> SEQ ID NO 46
<211> LENGTH: 19
<212> TYPE: PRT
<213> ORGANISM: Artificial Sequence
<220> FEATURE:
<223> OTHER INFORMATION: fusion protein

<400> SEQUENCE: 46

Lys Lys Gly His Ile Tyr Gln Gly Ser Glu Ala Asp Ser Val Phe Ser
1               5                   10                  15

Gly Phe Leu

<210> SEQ ID NO 47
<211> LENGTH: 19
<212> TYPE: PRT
<213> ORGANISM: Artificial Sequence
<220> FEATURE:
<223> OTHER INFORMATION: fusion protein

<400> SEQUENCE: 47

Lys Gly His Ile Tyr Gln Gly Ser Glu Ala Asp Ser Val Phe Ser Gly
1               5                   10                  15

Phe Leu Ile

<210> SEQ ID NO 48
<211> LENGTH: 19
<212> TYPE: PRT
<213> ORGANISM: Artificial Sequence
<220> FEATURE:
<223> OTHER INFORMATION: fusion protein

<400> SEQUENCE: 48

Gly His Ile Tyr Gln Gly Ser Glu Ala Asp Ser Val Phe Ser Gly Phe
1               5                   10                  15

Leu Ile Phe

<210> SEQ ID NO 49
<211> LENGTH: 19
<212> TYPE: PRT
<213> ORGANISM: Artificial Sequence
<220> FEATURE:
<223> OTHER INFORMATION: fusion protein
```

```
<400> SEQUENCE: 49

His Ile Tyr Gln Gly Ser Glu Ala Asp Ser Val Phe Ser Gly Phe Leu
1               5                   10                  15

Ile Phe Pro

<210> SEQ ID NO 50
<211> LENGTH: 19
<212> TYPE: PRT
<213> ORGANISM: Artificial Sequence
<220> FEATURE:
<223> OTHER INFORMATION: fusion protein

<400> SEQUENCE: 50

Ile Tyr Gln Gly Ser Glu Ala Asp Ser Val Phe Ser Gly Phe Leu Ile
1               5                   10                  15

Phe Pro Ser

<210> SEQ ID NO 51
<211> LENGTH: 19
<212> TYPE: PRT
<213> ORGANISM: Artificial Sequence
<220> FEATURE:
<223> OTHER INFORMATION: fusion protein

<400> SEQUENCE: 51

Tyr Gln Gly Ser Glu Ala Asp Ser Val Phe Ser Gly Phe Leu Ile Phe
1               5                   10                  15

Pro Ser Ala

<210> SEQ ID NO 52
<211> LENGTH: 17
<212> TYPE: PRT
<213> ORGANISM: Artificial Sequence
<220> FEATURE:
<223> OTHER INFORMATION: fusion protein

<400> SEQUENCE: 52

Asp Pro Lys Lys Gly His Ile Tyr Gln Gly Ser Glu Ala Asp Ser Val
1               5                   10                  15

Phe

<210> SEQ ID NO 53
<211> LENGTH: 17
<212> TYPE: PRT
<213> ORGANISM: Artificial Sequence
<220> FEATURE:
<223> OTHER INFORMATION: fusion protein

<400> SEQUENCE: 53

Pro Lys Lys Gly His Ile Tyr Gln Gly Ser Glu Ala Asp Ser Val Phe
1               5                   10                  15

Ser

<210> SEQ ID NO 54
<211> LENGTH: 17
<212> TYPE: PRT
<213> ORGANISM: Artificial Sequence
<220> FEATURE:
<223> OTHER INFORMATION: fusion protein

<400> SEQUENCE: 54

Lys Lys Gly His Ile Tyr Gln Gly Ser Glu Ala Asp Ser Val Phe Ser
1               5                   10                  15
```

Gly

<210> SEQ ID NO 55
<211> LENGTH: 17
<212> TYPE: PRT
<213> ORGANISM: Artificial Sequence
<220> FEATURE:
<223> OTHER INFORMATION: fusion protein

<400> SEQUENCE: 55

Lys Gly His Ile Tyr Gln Gly Ser Glu Ala Asp Ser Val Phe Ser Gly
1               5                   10                  15

Phe

<210> SEQ ID NO 56
<211> LENGTH: 17
<212> TYPE: PRT
<213> ORGANISM: Artificial Sequence
<220> FEATURE:
<223> OTHER INFORMATION: fusion protein

<400> SEQUENCE: 56

Gly His Ile Tyr Gln Gly Ser Glu Ala Asp Ser Val Phe Ser Gly Phe
1               5                   10                  15

Leu

<210> SEQ ID NO 57
<211> LENGTH: 17
<212> TYPE: PRT
<213> ORGANISM: Artificial Sequence
<220> FEATURE:
<223> OTHER INFORMATION: fusion protein

<400> SEQUENCE: 57

His Ile Tyr Gln Gly Ser Glu Ala Asp Ser Val Phe Ser Gly Phe Leu
1               5                   10                  15

Ile

<210> SEQ ID NO 58
<211> LENGTH: 17
<212> TYPE: PRT
<213> ORGANISM: Artificial Sequence
<220> FEATURE:
<223> OTHER INFORMATION: fusion protein

<400> SEQUENCE: 58

Ile Tyr Gln Gly Ser Glu Ala Asp Ser Val Phe Ser Gly Phe Leu Ile
1               5                   10                  15

Phe

<210> SEQ ID NO 59
<211> LENGTH: 17
<212> TYPE: PRT
<213> ORGANISM: Artificial Sequence
<220> FEATURE:
<223> OTHER INFORMATION: fusion protein

<400> SEQUENCE: 59

Tyr Gln Gly Ser Glu Ala Asp Ser Val Phe Ser Gly Phe Leu Ile Phe
1               5                   10                  15

Pro

```
<210> SEQ ID NO 60
<211> LENGTH: 17
<212> TYPE: PRT
<213> ORGANISM: Artificial Sequence
<220> FEATURE:
<223> OTHER INFORMATION: fusion protein

<400> SEQUENCE: 60

Gln Gly Ser Glu Ala Asp Ser Val Phe Ser Gly Phe Leu Ile Phe Pro
1               5                   10                  15
Ser

<210> SEQ ID NO 61
<211> LENGTH: 17
<212> TYPE: PRT
<213> ORGANISM: Artificial Sequence
<220> FEATURE:
<223> OTHER INFORMATION: fusion protein

<400> SEQUENCE: 61

Gly Ser Glu Ala Asp Ser Val Phe Ser Gly Phe Leu Ile Phe Pro Ser
1               5                   10                  15
Ala

<210> SEQ ID NO 62
<211> LENGTH: 16
<212> TYPE: PRT
<213> ORGANISM: Artificial Sequence
<220> FEATURE:
<223> OTHER INFORMATION: fusion protein

<400> SEQUENCE: 62

Pro Lys Lys Gly His Ile Tyr Gln Gly Ser Glu Ala Asp Ser Val Phe
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: fusion protein

<400> SEQUENCE: 63

Lys Lys Gly His Ile Tyr Gln Gly Ser Glu Ala Asp Ser Val Phe Ser
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: fusion protein

<400> SEQUENCE: 64

Lys Gly His Ile Tyr Gln Gly Ser Glu Ala Asp Ser Val Phe Ser Gly
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: fusion protein

<400> SEQUENCE: 65

Gly His Ile Tyr Gln Gly Ser Glu Ala Asp Ser Val Phe Ser Gly Phe
```

<210> SEQ ID NO 66
<211> LENGTH: 16
<212> TYPE: PRT
<213> ORGANISM: Artificial Sequence
<220> FEATURE:
<223> OTHER INFORMATION: fusion protein

<400> SEQUENCE: 66

```
His Ile Tyr Gln Gly Ser Glu Ala Asp Ser Val Phe Ser Gly Phe Leu
1               5                   10                  15
```

<210> SEQ ID NO 67
<211> LENGTH: 16
<212> TYPE: PRT
<213> ORGANISM: Artificial Sequence
<220> FEATURE:
<223> OTHER INFORMATION: fusion protein

<400> SEQUENCE: 67

```
Ile Tyr Gln Gly Ser Glu Ala Asp Ser Val Phe Ser Gly Phe Leu Ile
1               5                   10                  15
```

<210> SEQ ID NO 68
<211> LENGTH: 16
<212> TYPE: PRT
<213> ORGANISM: Artificial Sequence
<220> FEATURE:
<223> OTHER INFORMATION: fusion protein

<400> SEQUENCE: 68

```
Tyr Gln Gly Ser Glu Ala Asp Ser Val Phe Ser Gly Phe Leu Ile Phe
1               5                   10                  15
```

<210> SEQ ID NO 69
<211> LENGTH: 16
<212> TYPE: PRT
<213> ORGANISM: Artificial Sequence
<220> FEATURE:
<223> OTHER INFORMATION: fusion protein

<400> SEQUENCE: 69

```
Gln Gly Ser Glu Ala Asp Ser Val Phe Ser Gly Phe Leu Ile Phe Pro
1               5                   10                  15
```

<210> SEQ ID NO 70
<211> LENGTH: 16
<212> TYPE: PRT
<213> ORGANISM: Artificial Sequence
<220> FEATURE:
<223> OTHER INFORMATION: fusion protein

<400> SEQUENCE: 70

```
Gly Ser Glu Ala Asp Ser Val Phe Ser Gly Phe Leu Ile Phe Pro Ser
1               5                   10                  15
```

<210> SEQ ID NO 71
<211> LENGTH: 16
<212> TYPE: PRT
<213> ORGANISM: Artificial Sequence
<220> FEATURE:
<223> OTHER INFORMATION: fusion protein

<400> SEQUENCE: 71

```
Ser Glu Ala Asp Ser Val Phe Ser Gly Phe Leu Ile Phe Pro Ser Ala
1               5                   10                  15
```

```
<210> SEQ ID NO 72
<211> LENGTH: 15
<212> TYPE: PRT
<213> ORGANISM: Artificial Sequence
<220> FEATURE:
<223> OTHER INFORMATION: fusion protein

<400> SEQUENCE: 72

Lys Lys Gly His Ile Tyr Gln Gly Ser Glu Ala Asp Ser Val Phe
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: fusion protein

<400> SEQUENCE: 73

Lys Gly His Ile Tyr Gln Gly Ser Glu Ala Asp Ser Val Phe Ser
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: fusion protein

<400> SEQUENCE: 74

Gly His Ile Tyr Gln Gly Ser Glu Ala Asp Ser Val Phe Ser Gly
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: fusion protein

<400> SEQUENCE: 75

His Ile Tyr Gln Gly Ser Glu Ala Asp Ser Val Phe Ser Gly Phe
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: fusion protein

<400> SEQUENCE: 76

Ile Tyr Gln Gly Ser Glu Ala Asp Ser Val Phe Ser Gly Phe Leu
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: fusion protein

<400> SEQUENCE: 77

Tyr Gln Gly Ser Glu Ala Asp Ser Val Phe Ser Gly Phe Leu Ile
1               5                   10                  15
```

```
<210> SEQ ID NO 78
<211> LENGTH: 15
<212> TYPE: PRT
<213> ORGANISM: Artificial Sequence
<220> FEATURE:
<223> OTHER INFORMATION: fusion protein

<400> SEQUENCE: 78

Gln Gly Ser Glu Ala Asp Ser Val Phe Ser Gly Phe Leu Ile Phe
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: fusion protein

<400> SEQUENCE: 79

Gly Ser Glu Ala Asp Ser Val Phe Ser Gly Phe Leu Ile Phe Pro
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: fusion protein

<400> SEQUENCE: 80

Ser Glu Ala Asp Ser Val Phe Ser Gly Phe Leu Ile Phe Pro Ser
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: fusion protein

<400> SEQUENCE: 81

Glu Ala Asp Ser Val Phe Ser Gly Phe Leu Ile Phe Pro Ser Ala
1               5                   10                  15

<210> SEQ ID NO 82
<211> LENGTH: 13
<212> TYPE: PRT
<213> ORGANISM: Artificial Sequence
<220> FEATURE:
<223> OTHER INFORMATION: fusion protein

<400> SEQUENCE: 82

Gly His Ile Tyr Gln Gly Ser Glu Ala Asp Ser Val Phe
1               5                   10

<210> SEQ ID NO 83
<211> LENGTH: 13
<212> TYPE: PRT
<213> ORGANISM: Artificial Sequence
<220> FEATURE:
<223> OTHER INFORMATION: fusion protein

<400> SEQUENCE: 83

His Ile Tyr Gln Gly Ser Glu Ala Asp Ser Val Phe Ser
1               5                   10
```

```
<210> SEQ ID NO 84
<211> LENGTH: 13
<212> TYPE: PRT
<213> ORGANISM: Artificial Sequence
<220> FEATURE:
<223> OTHER INFORMATION: fusion protein

<400> SEQUENCE: 84

Ile Tyr Gln Gly Ser Glu Ala Asp Ser Val Phe Ser Gly
1               5                   10

<210> SEQ ID NO 85
<211> LENGTH: 13
<212> TYPE: PRT
<213> ORGANISM: Artificial Sequence
<220> FEATURE:
<223> OTHER INFORMATION: fusion protein

<400> SEQUENCE: 85

Tyr Gln Gly Ser Glu Ala Asp Ser Val Phe Ser Gly Phe
1               5                   10

<210> SEQ ID NO 86
<211> LENGTH: 13
<212> TYPE: PRT
<213> ORGANISM: Artificial Sequence
<220> FEATURE:
<223> OTHER INFORMATION: fusion protein

<400> SEQUENCE: 86

Gln Gly Ser Glu Ala Asp Ser Val Phe Ser Gly Phe Leu
1               5                   10

<210> SEQ ID NO 87
<211> LENGTH: 13
<212> TYPE: PRT
<213> ORGANISM: Artificial Sequence
<220> FEATURE:
<223> OTHER INFORMATION: fusion protein

<400> SEQUENCE: 87

Gly Ser Glu Ala Asp Ser Val Phe Ser Gly Phe Leu Ile
1               5                   10

<210> SEQ ID NO 88
<211> LENGTH: 13
<212> TYPE: PRT
<213> ORGANISM: Artificial Sequence
<220> FEATURE:
<223> OTHER INFORMATION: fusion protein

<400> SEQUENCE: 88

Ser Glu Ala Asp Ser Val Phe Ser Gly Phe Leu Ile Phe
1               5                   10

<210> SEQ ID NO 89
<211> LENGTH: 13
<212> TYPE: PRT
<213> ORGANISM: Artificial Sequence
<220> FEATURE:
<223> OTHER INFORMATION: fusion protein

<400> SEQUENCE: 89

Glu Ala Asp Ser Val Phe Ser Gly Phe Leu Ile Phe Pro
1               5                   10

<210> SEQ ID NO 90
```

```
<211> LENGTH: 12
<212> TYPE: PRT
<213> ORGANISM: Artificial Sequence
<220> FEATURE:
<223> OTHER INFORMATION: fusion protein

<400> SEQUENCE: 90

His Ile Tyr Gln Gly Ser Glu Ala Asp Ser Val Phe
1               5                   10

<210> SEQ ID NO 91
<211> LENGTH: 12
<212> TYPE: PRT
<213> ORGANISM: Artificial Sequence
<220> FEATURE:
<223> OTHER INFORMATION: fusion protein

<400> SEQUENCE: 91

Ile Tyr Gln Gly Ser Glu Ala Asp Ser Val Phe Ser
1               5                   10

<210> SEQ ID NO 92
<211> LENGTH: 12
<212> TYPE: PRT
<213> ORGANISM: Artificial Sequence
<220> FEATURE:
<223> OTHER INFORMATION: fusion protein

<400> SEQUENCE: 92

Tyr Gln Gly Ser Glu Ala Asp Ser Val Phe Ser Gly
1               5                   10

<210> SEQ ID NO 93
<211> LENGTH: 12
<212> TYPE: PRT
<213> ORGANISM: Artificial Sequence
<220> FEATURE:
<223> OTHER INFORMATION: fusion protein

<400> SEQUENCE: 93

Gln Gly Ser Glu Ala Asp Ser Val Phe Ser Gly Phe
1               5                   10

<210> SEQ ID NO 94
<211> LENGTH: 12
<212> TYPE: PRT
<213> ORGANISM: Artificial Sequence
<220> FEATURE:
<223> OTHER INFORMATION: fusion protein

<400> SEQUENCE: 94

Gly Ser Glu Ala Asp Ser Val Phe Ser Gly Phe Leu
1               5                   10

<210> SEQ ID NO 95
<211> LENGTH: 12
<212> TYPE: PRT
<213> ORGANISM: Artificial Sequence
<220> FEATURE:
<223> OTHER INFORMATION: fusion protein

<400> SEQUENCE: 95

Ser Glu Ala Asp Ser Val Phe Ser Gly Phe Leu Ile
1               5                   10

<210> SEQ ID NO 96
<211> LENGTH: 12
```

```
<212> TYPE: PRT
<213> ORGANISM: Artificial Sequence
<220> FEATURE:
<223> OTHER INFORMATION: fusion protein

<400> SEQUENCE: 96

Glu Ala Asp Ser Val Phe Ser Gly Phe Leu Ile Phe
1               5                   10

<210> SEQ ID NO 97
<211> LENGTH: 11
<212> TYPE: PRT
<213> ORGANISM: Artificial Sequence
<220> FEATURE:
<223> OTHER INFORMATION: fusion protein

<400> SEQUENCE: 97

Ile Tyr Gln Gly Ser Glu Ala Asp Ser Val Phe
1               5                   10

<210> SEQ ID NO 98
<211> LENGTH: 11
<212> TYPE: PRT
<213> ORGANISM: Artificial Sequence
<220> FEATURE:
<223> OTHER INFORMATION: fusion protein

<400> SEQUENCE: 98

Tyr Gln Gly Ser Glu Ala Asp Ser Val Phe Ser
1               5                   10

<210> SEQ ID NO 99
<211> LENGTH: 11
<212> TYPE: PRT
<213> ORGANISM: Artificial Sequence
<220> FEATURE:
<223> OTHER INFORMATION: fusion protein

<400> SEQUENCE: 99

Gln Gly Ser Glu Ala Asp Ser Val Phe Ser Gly
1               5                   10

<210> SEQ ID NO 100
<211> LENGTH: 11
<212> TYPE: PRT
<213> ORGANISM: Artificial Sequence
<220> FEATURE:
<223> OTHER INFORMATION: fusion protein

<400> SEQUENCE: 100

Gly Ser Glu Ala Asp Ser Val Phe Ser Gly Phe
1               5                   10

<210> SEQ ID NO 101
<211> LENGTH: 11
<212> TYPE: PRT
<213> ORGANISM: Artificial Sequence
<220> FEATURE:
<223> OTHER INFORMATION: fusion protein

<400> SEQUENCE: 101

Ser Glu Ala Asp Ser Val Phe Ser Gly Phe Leu
1               5                   10

<210> SEQ ID NO 102
<211> LENGTH: 11
<212> TYPE: PRT
```

```
<213> ORGANISM: Artificial Sequence
<220> FEATURE:
<223> OTHER INFORMATION: fusion protein

<400> SEQUENCE: 102

Glu Ala Asp Ser Val Phe Ser Gly Phe Leu Ile
1               5                   10

<210> SEQ ID NO 103
<211> LENGTH: 10
<212> TYPE: PRT
<213> ORGANISM: Artificial Sequence
<220> FEATURE:
<223> OTHER INFORMATION: fusion protein

<400> SEQUENCE: 103

Tyr Gln Gly Ser Glu Ala Asp Ser Val Phe
1               5                   10

<210> SEQ ID NO 104
<211> LENGTH: 10
<212> TYPE: PRT
<213> ORGANISM: Artificial Sequence
<220> FEATURE:
<223> OTHER INFORMATION: fusion protein

<400> SEQUENCE: 104

Gln Gly Ser Glu Ala Asp Ser Val Phe Ser
1               5                   10

<210> SEQ ID NO 105
<211> LENGTH: 10
<212> TYPE: PRT
<213> ORGANISM: Artificial Sequence
<220> FEATURE:
<223> OTHER INFORMATION: fusion protein

<400> SEQUENCE: 105

Gly Ser Glu Ala Asp Ser Val Phe Ser Gly
1               5                   10

<210> SEQ ID NO 106
<211> LENGTH: 10
<212> TYPE: PRT
<213> ORGANISM: Artificial Sequence
<220> FEATURE:
<223> OTHER INFORMATION: fusion protein

<400> SEQUENCE: 106

Ser Glu Ala Asp Ser Val Phe Ser Gly Phe
1               5                   10

<210> SEQ ID NO 107
<211> LENGTH: 10
<212> TYPE: PRT
<213> ORGANISM: Artificial Sequence
<220> FEATURE:
<223> OTHER INFORMATION: fusion protein

<400> SEQUENCE: 107

Glu Ala Asp Ser Val Phe Ser Gly Phe Leu
1               5                   10

<210> SEQ ID NO 108
<211> LENGTH: 9
<212> TYPE: PRT
<213> ORGANISM: Artificial Sequence
```

```
<220> FEATURE:
<223> OTHER INFORMATION: fusion portein

<400> SEQUENCE: 108

Gln Gly Ser Glu Ala Asp Ser Val Phe
1               5

<210> SEQ ID NO 109
<211> LENGTH: 9
<212> TYPE: PRT
<213> ORGANISM: Artificial Sequence
<220> FEATURE:
<223> OTHER INFORMATION: fusion protein

<400> SEQUENCE: 109

Gly Ser Glu Ala Asp Ser Val Phe Ser
1               5

<210> SEQ ID NO 110
<211> LENGTH: 9
<212> TYPE: PRT
<213> ORGANISM: Artificial Sequence
<220> FEATURE:
<223> OTHER INFORMATION: fusion protein

<400> SEQUENCE: 110

Ser Glu Ala Asp Ser Val Phe Ser Gly
1               5

<210> SEQ ID NO 111
<211> LENGTH: 9
<212> TYPE: PRT
<213> ORGANISM: Artificial Sequence
<220> FEATURE:
<223> OTHER INFORMATION: fusion protein

<400> SEQUENCE: 111

Glu Ala Asp Ser Val Phe Ser Gly Phe
1               5

<210> SEQ ID NO 112
<211> LENGTH: 8
<212> TYPE: PRT
<213> ORGANISM: Artificial Sequence
<220> FEATURE:
<223> OTHER INFORMATION: fusion protein

<400> SEQUENCE: 112

Gly Ser Glu Ala Asp Ser Val Phe
1               5

<210> SEQ ID NO 113
<211> LENGTH: 8
<212> TYPE: PRT
<213> ORGANISM: Artificial Sequence
<220> FEATURE:
<223> OTHER INFORMATION: fusion protein

<400> SEQUENCE: 113

Ser Glu Ala Asp Ser Val Phe Ser
1               5

<210> SEQ ID NO 114
<211> LENGTH: 8
<212> TYPE: PRT
<213> ORGANISM: Artificial Sequence
<220> FEATURE:
```

```
<223> OTHER INFORMATION: fusion protein

<400> SEQUENCE: 114

Glu Ala Asp Ser Val Phe Ser Gly
1               5

<210> SEQ ID NO 115
<211> LENGTH: 7
<212> TYPE: PRT
<213> ORGANISM: Artificial Sequence
<220> FEATURE:
<223> OTHER INFORMATION: fusion protein

<400> SEQUENCE: 115

Ser Glu Ala Asp Ser Val Phe
1               5

<210> SEQ ID NO 116
<211> LENGTH: 7
<212> TYPE: PRT
<213> ORGANISM: Artificial Sequence
<220> FEATURE:
<223> OTHER INFORMATION: fusion protein

<400> SEQUENCE: 116

Glu Ala Asp Ser Val Phe Ser
1               5

<210> SEQ ID NO 117
<211> LENGTH: 20
<212> TYPE: PRT
<213> ORGANISM: Artificial Sequence
<220> FEATURE:
<223> OTHER INFORMATION: fusion protein

<400> SEQUENCE: 117

Met Val Thr Glu Asp Leu Cys Arg Ala Pro Asp Gly Lys Lys Gly Glu
1               5                   10                  15

Ala Gly Arg Pro
            20

<210> SEQ ID NO 118
<211> LENGTH: 19
<212> TYPE: PRT
<213> ORGANISM: Artificial Sequence
<220> FEATURE:
<223> OTHER INFORMATION: fusion protein

<400> SEQUENCE: 118

Val Thr Glu Asp Leu Cys Arg Ala Pro Asp Gly Lys Lys Gly Glu Ala
1               5                   10                  15

Gly Arg Pro

<210> SEQ ID NO 119
<211> LENGTH: 18
<212> TYPE: PRT
<213> ORGANISM: Artificial Sequence
<220> FEATURE:
<223> OTHER INFORMATION: fusion protein

<400> SEQUENCE: 119

Thr Glu Asp Leu Cys Arg Ala Pro Asp Gly Lys Lys Gly Glu Ala Gly
1               5                   10                  15

Arg Pro
```

```
<210> SEQ ID NO 120
<211> LENGTH: 17
<212> TYPE: PRT
<213> ORGANISM: Artificial Sequence
<220> FEATURE:
<223> OTHER INFORMATION: fusion protein

<400> SEQUENCE: 120

Glu Asp Leu Cys Arg Ala Pro Asp Gly Lys Lys Gly Glu Ala Gly Arg
1               5                   10                  15

Pro

<210> SEQ ID NO 121
<211> LENGTH: 16
<212> TYPE: PRT
<213> ORGANISM: Artificial Sequence
<220> FEATURE:
<223> OTHER INFORMATION: fusion protein

<400> SEQUENCE: 121

Asp Leu Cys Arg Ala Pro Asp Gly Lys Lys Gly Glu Ala Gly Arg Pro
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: fusion protein

<400> SEQUENCE: 122

Leu Cys Arg Ala Pro Asp Gly Lys Lys Gly Glu Ala Gly Arg Pro
1               5                   10                  15

<210> SEQ ID NO 123
<211> LENGTH: 14
<212> TYPE: PRT
<213> ORGANISM: Artificial Sequence
<220> FEATURE:
<223> OTHER INFORMATION: fusion protein

<400> SEQUENCE: 123

Cys Arg Ala Pro Asp Gly Lys Lys Gly Glu Ala Gly Arg Pro
1               5                   10

<210> SEQ ID NO 124
<211> LENGTH: 13
<212> TYPE: PRT
<213> ORGANISM: Artificial Sequence
<220> FEATURE:
<223> OTHER INFORMATION: fusion protein

<400> SEQUENCE: 124

Arg Ala Pro Asp Gly Lys Lys Gly Glu Ala Gly Arg Pro
1               5                   10

<210> SEQ ID NO 125
<211> LENGTH: 12
<212> TYPE: PRT
<213> ORGANISM: Artificial Sequence
<220> FEATURE:
<223> OTHER INFORMATION: fusion protein

<400> SEQUENCE: 125

Ala Pro Asp Gly Lys Lys Gly Glu Ala Gly Arg Pro
1               5                   10
```

<210> SEQ ID NO 126
<211> LENGTH: 11
<212> TYPE: PRT
<213> ORGANISM: Artificial Sequence
<220> FEATURE:
<223> OTHER INFORMATION: fusion protein

<400> SEQUENCE: 126

Pro Asp Gly Lys Lys Gly Glu Ala Gly Arg Pro
1               5                   10

<210> SEQ ID NO 127
<211> LENGTH: 10
<212> TYPE: PRT
<213> ORGANISM: Artificial Sequence
<220> FEATURE:
<223> OTHER INFORMATION: fusion protein

<400> SEQUENCE: 127

Asp Gly Lys Lys Gly Glu Ala Gly Arg Pro
1               5                   10

<210> SEQ ID NO 128
<211> LENGTH: 9
<212> TYPE: PRT
<213> ORGANISM: Artificial Sequence
<220> FEATURE:
<223> OTHER INFORMATION: fusion protein

<400> SEQUENCE: 128

Gly Lys Lys Gly Glu Ala Gly Arg Pro
1               5

<210> SEQ ID NO 129
<211> LENGTH: 8
<212> TYPE: PRT
<213> ORGANISM: Artificial Sequence
<220> FEATURE:
<223> OTHER INFORMATION: fusion protein

<400> SEQUENCE: 129

Lys Lys Gly Glu Ala Gly Arg Pro
1               5

<210> SEQ ID NO 130
<211> LENGTH: 7
<212> TYPE: PRT
<213> ORGANISM: Artificial Sequence
<220> FEATURE:
<223> OTHER INFORMATION: fusion protein

<400> SEQUENCE: 130

Lys Gly Glu Ala Gly Arg Pro
1               5

<210> SEQ ID NO 131
<211> LENGTH: 6
<212> TYPE: PRT
<213> ORGANISM: Artificial Sequence
<220> FEATURE:
<223> OTHER INFORMATION: fusion protein

<400> SEQUENCE: 131

Gly Glu Ala Gly Arg Pro
1               5

<210> SEQ ID NO 132
<211> LENGTH: 20
<212> TYPE: PRT
<213> ORGANISM: Artificial Sequence
<220> FEATURE:
<223> OTHER INFORMATION: fusion protein

<400> SEQUENCE: 132

Glu Ala Gly Arg Pro Gly Arg Arg Gly Arg Pro Gly Leu Lys Gly Glu
1               5                   10                  15

Gln Gly Glu Pro
            20

<210> SEQ ID NO 133
<211> LENGTH: 19
<212> TYPE: PRT
<213> ORGANISM: Artificial Sequence
<220> FEATURE:
<223> OTHER INFORMATION: fusion protein

<400> SEQUENCE: 133

Glu Ala Gly Arg Pro Gly Arg Arg Gly Arg Pro Gly Leu Lys Gly Glu
1               5                   10                  15

Gln Gly Glu

<210> SEQ ID NO 134
<211> LENGTH: 18
<212> TYPE: PRT
<213> ORGANISM: Artificial Sequence
<220> FEATURE:
<223> OTHER INFORMATION: fusion protein

<400> SEQUENCE: 134

Glu Ala Gly Arg Pro Gly Arg Arg Gly Arg Pro Gly Leu Lys Gly Glu
1               5                   10                  15

Gln Gly

<210> SEQ ID NO 135
<211> LENGTH: 17
<212> TYPE: PRT
<213> ORGANISM: Artificial Sequence
<220> FEATURE:
<223> OTHER INFORMATION: fusion protein

<400> SEQUENCE: 135

Glu Ala Gly Arg Pro Gly Arg Arg Gly Arg Pro Gly Leu Lys Gly Glu
1               5                   10                  15

Gln

<210> SEQ ID NO 136
<211> LENGTH: 16
<212> TYPE: PRT
<213> ORGANISM: Artificial Sequence
<220> FEATURE:
<223> OTHER INFORMATION: fusion protein

<400> SEQUENCE: 136

Glu Ala Gly Arg Pro Gly Arg Arg Gly Arg Pro Gly Leu Lys Gly Glu
1               5                   10                  15

<210> SEQ ID NO 137
<211> LENGTH: 15
<212> TYPE: PRT
<213> ORGANISM: Artificial Sequence

```
<220> FEATURE:
<223> OTHER INFORMATION: fusion protein

<400> SEQUENCE: 137

Glu Ala Gly Arg Pro Gly Arg Arg Gly Arg Pro Gly Leu Lys Gly
1               5                   10                  15

<210> SEQ ID NO 138
<211> LENGTH: 14
<212> TYPE: PRT
<213> ORGANISM: Artificial Sequence
<220> FEATURE:
<223> OTHER INFORMATION: fusion protein

<400> SEQUENCE: 138

Glu Ala Gly Arg Pro Gly Arg Arg Gly Arg Pro Gly Leu Lys
1               5                   10

<210> SEQ ID NO 139
<211> LENGTH: 14
<212> TYPE: PRT
<213> ORGANISM: Artificial Sequence
<220> FEATURE:
<223> OTHER INFORMATION: fusion protein

<400> SEQUENCE: 139

Glu Ala Gly Arg Pro Gly Arg Arg Gly Arg Pro Gly Leu Lys
1               5                   10

<210> SEQ ID NO 140
<211> LENGTH: 13
<212> TYPE: PRT
<213> ORGANISM: Artificial Sequence
<220> FEATURE:
<223> OTHER INFORMATION: fusion protein

<400> SEQUENCE: 140

Glu Ala Gly Arg Pro Gly Arg Arg Gly Arg Pro Gly Leu
1               5                   10

<210> SEQ ID NO 141
<211> LENGTH: 12
<212> TYPE: PRT
<213> ORGANISM: Artificial Sequence
<220> FEATURE:
<223> OTHER INFORMATION: fusion protein

<400> SEQUENCE: 141

Glu Ala Gly Arg Pro Gly Arg Arg Gly Arg Pro Gly
1               5                   10

<210> SEQ ID NO 142
<211> LENGTH: 11
<212> TYPE: PRT
<213> ORGANISM: Artificial Sequence
<220> FEATURE:
<223> OTHER INFORMATION: fusion protein

<400> SEQUENCE: 142

Glu Ala Gly Arg Pro Gly Arg Arg Gly Arg Pro
1               5                   10

<210> SEQ ID NO 143
<211> LENGTH: 10
<212> TYPE: PRT
<213> ORGANISM: Artificial Sequence
<220> FEATURE:
```

```
<223> OTHER INFORMATION: fusion protein

<400> SEQUENCE: 143

Glu Ala Gly Arg Pro Gly Arg Arg Gly Arg
1               5                   10

<210> SEQ ID NO 144
<211> LENGTH: 9
<212> TYPE: PRT
<213> ORGANISM: Artificial Sequence
<220> FEATURE:
<223> OTHER INFORMATION: fusion protein

<400> SEQUENCE: 144

Glu Ala Gly Arg Pro Gly Arg Arg Gly
1               5

<210> SEQ ID NO 145
<211> LENGTH: 8
<212> TYPE: PRT
<213> ORGANISM: Artificial Sequence
<220> FEATURE:
<223> OTHER INFORMATION: fusion protein

<400> SEQUENCE: 145

Glu Ala Gly Arg Pro Gly Arg Arg
1               5

<210> SEQ ID NO 146
<211> LENGTH: 7
<212> TYPE: PRT
<213> ORGANISM: Artificial Sequence
<220> FEATURE:
<223> OTHER INFORMATION: fusion protein

<400> SEQUENCE: 146

Glu Ala Gly Arg Pro Gly Arg
1               5

<210> SEQ ID NO 147
<211> LENGTH: 6
<212> TYPE: PRT
<213> ORGANISM: Artificial Sequence
<220> FEATURE:
<223> OTHER INFORMATION: fusion protein

<400> SEQUENCE: 147

Glu Ala Gly Arg Pro Gly
1               5

<210> SEQ ID NO 148
<211> LENGTH: 20
<212> TYPE: PRT
<213> ORGANISM: Artificial Sequence
<220> FEATURE:
<223> OTHER INFORMATION: fusion protein

<400> SEQUENCE: 148

Val Thr Glu Asp Leu Cys Arg Ala Pro Asp Gly Lys Lys Gly Glu Ala
1               5                   10                  15

Gly Arg Pro Gly
            20

<210> SEQ ID NO 149
<211> LENGTH: 20
<212> TYPE: PRT
```

```
<213> ORGANISM: Artificial Sequence
<220> FEATURE:
<223> OTHER INFORMATION: fusion protein

<400> SEQUENCE: 149

Thr Glu Asp Leu Cys Arg Ala Pro Asp Gly Lys Lys Gly Glu Ala Gly
1               5                   10                  15

Arg Pro Gly Arg
            20

<210> SEQ ID NO 150
<211> LENGTH: 20
<212> TYPE: PRT
<213> ORGANISM: Artificial Sequence
<220> FEATURE:
<223> OTHER INFORMATION: fusion protein

<400> SEQUENCE: 150

Glu Asp Leu Cys Arg Ala Pro Asp Gly Lys Lys Gly Glu Ala Gly Arg
1               5                   10                  15

Pro Gly Arg Arg
            20

<210> SEQ ID NO 151
<211> LENGTH: 20
<212> TYPE: PRT
<213> ORGANISM: Artificial Sequence
<220> FEATURE:
<223> OTHER INFORMATION: fusion protein

<400> SEQUENCE: 151

Asp Leu Cys Arg Ala Pro Asp Gly Lys Lys Gly Glu Ala Gly Arg Pro
1               5                   10                  15

Gly Arg Arg Gly
            20

<210> SEQ ID NO 152
<211> LENGTH: 20
<212> TYPE: PRT
<213> ORGANISM: Artificial Sequence
<220> FEATURE:
<223> OTHER INFORMATION: fusion protein

<400> SEQUENCE: 152

Leu Cys Arg Ala Pro Asp Gly Lys Lys Gly Glu Ala Gly Arg Pro Gly
1               5                   10                  15

Arg Arg Gly Arg
            20

<210> SEQ ID NO 153
<211> LENGTH: 20
<212> TYPE: PRT
<213> ORGANISM: Artificial Sequence
<220> FEATURE:
<223> OTHER INFORMATION: fusion protein

<400> SEQUENCE: 153

Cys Arg Ala Pro Asp Gly Lys Lys Gly Glu Ala Gly Arg Pro Gly Arg
1               5                   10                  15

Arg Gly Arg Pro
            20

<210> SEQ ID NO 154
<211> LENGTH: 20
```

```
<212> TYPE: PRT
<213> ORGANISM: Artificial Sequence
<220> FEATURE:
<223> OTHER INFORMATION: fusion protein

<400> SEQUENCE: 154

Arg Ala Pro Asp Gly Lys Lys Gly Glu Ala Gly Arg Pro Gly Arg Arg
1               5                   10                  15

Gly Arg Pro Gly
            20

<210> SEQ ID NO 155
<211> LENGTH: 20
<212> TYPE: PRT
<213> ORGANISM: Artificial Sequence
<220> FEATURE:
<223> OTHER INFORMATION: fusion protein

<400> SEQUENCE: 155

Ala Pro Asp Gly Lys Lys Gly Glu Ala Gly Arg Pro Gly Arg Arg Gly
1               5                   10                  15

Arg Pro Gly Leu
            20

<210> SEQ ID NO 156
<211> LENGTH: 20
<212> TYPE: PRT
<213> ORGANISM: Artificial Sequence
<220> FEATURE:
<223> OTHER INFORMATION: fusion protein

<400> SEQUENCE: 156

Pro Asp Gly Lys Lys Gly Glu Ala Gly Arg Pro Gly Arg Arg Gly Arg
1               5                   10                  15

Pro Gly Leu Lys
            20

<210> SEQ ID NO 157
<211> LENGTH: 20
<212> TYPE: PRT
<213> ORGANISM: Artificial Sequence
<220> FEATURE:
<223> OTHER INFORMATION: fusion protein

<400> SEQUENCE: 157

Asp Gly Lys Lys Gly Glu Ala Gly Arg Pro Gly Arg Arg Gly Arg Pro
1               5                   10                  15

Gly Leu Lys Gly
            20

<210> SEQ ID NO 158
<211> LENGTH: 20
<212> TYPE: PRT
<213> ORGANISM: Artificial Sequence
<220> FEATURE:
<223> OTHER INFORMATION: fusion protein

<400> SEQUENCE: 158

Gly Lys Lys Gly Glu Ala Gly Arg Pro Gly Arg Arg Gly Arg Pro Gly
1               5                   10                  15

Leu Lys Gly Glu
            20

<210> SEQ ID NO 159
```

```
<211> LENGTH: 20
<212> TYPE: PRT
<213> ORGANISM: Artificial Sequence
<220> FEATURE:
<223> OTHER INFORMATION: fusion protein

<400> SEQUENCE: 159

Lys Lys Gly Glu Ala Gly Arg Pro Gly Arg Arg Gly Arg Pro Gly Leu
1               5                   10                  15

Lys Gly Glu Gln
            20

<210> SEQ ID NO 160
<211> LENGTH: 20
<212> TYPE: PRT
<213> ORGANISM: Artificial Sequence
<220> FEATURE:
<223> OTHER INFORMATION: fusion protein

<400> SEQUENCE: 160

Lys Gly Glu Ala Gly Arg Pro Gly Arg Arg Gly Arg Pro Gly Leu Lys
1               5                   10                  15

Gly Glu Gln Gly
            20

<210> SEQ ID NO 161
<211> LENGTH: 20
<212> TYPE: PRT
<213> ORGANISM: Artificial Sequence
<220> FEATURE:
<223> OTHER INFORMATION: fusion protein

<400> SEQUENCE: 161

Gly Glu Ala Gly Arg Pro Gly Arg Arg Gly Arg Pro Gly Leu Lys Gly
1               5                   10                  15

Glu Gln Gly Glu
            20

<210> SEQ ID NO 162
<211> LENGTH: 18
<212> TYPE: PRT
<213> ORGANISM: Artificial Sequence
<220> FEATURE:
<223> OTHER INFORMATION: fusion protein

<400> SEQUENCE: 162

Glu Asp Leu Cys Arg Ala Pro Asp Gly Lys Lys Gly Glu Ala Gly Arg
1               5                   10                  15

Pro Gly

<210> SEQ ID NO 163
<211> LENGTH: 18
<212> TYPE: PRT
<213> ORGANISM: Artificial Sequence
<220> FEATURE:
<223> OTHER INFORMATION: fusion protein

<400> SEQUENCE: 163

Asp Leu Cys Arg Ala Pro Asp Gly Lys Lys Gly Glu Ala Gly Arg Pro
1               5                   10                  15

Gly Arg

<210> SEQ ID NO 164
<211> LENGTH: 18
```

```
<212> TYPE: PRT
<213> ORGANISM: Artificial Sequence
<220> FEATURE:
<223> OTHER INFORMATION: fusion protein

<400> SEQUENCE: 164

Leu Cys Arg Ala Pro Asp Gly Lys Lys Gly Glu Ala Gly Arg Pro Gly
1               5                   10                  15

Arg Arg

<210> SEQ ID NO 165
<211> LENGTH: 18
<212> TYPE: PRT
<213> ORGANISM: Artificial Sequence
<220> FEATURE:
<223> OTHER INFORMATION: fusion protein

<400> SEQUENCE: 165

Cys Arg Ala Pro Asp Gly Lys Lys Gly Glu Ala Gly Arg Pro Gly Arg
1               5                   10                  15

Arg Gly

<210> SEQ ID NO 166
<211> LENGTH: 18
<212> TYPE: PRT
<213> ORGANISM: Artificial Sequence
<220> FEATURE:
<223> OTHER INFORMATION: fusion protein

<400> SEQUENCE: 166

Arg Ala Pro Asp Gly Lys Lys Gly Glu Ala Gly Arg Pro Gly Arg Arg
1               5                   10                  15

Gly Arg

<210> SEQ ID NO 167
<211> LENGTH: 18
<212> TYPE: PRT
<213> ORGANISM: Artificial Sequence
<220> FEATURE:
<223> OTHER INFORMATION: fusion protein

<400> SEQUENCE: 167

Ala Pro Asp Gly Lys Lys Gly Glu Ala Gly Arg Pro Gly Arg Arg Gly
1               5                   10                  15

Arg Pro

<210> SEQ ID NO 168
<211> LENGTH: 18
<212> TYPE: PRT
<213> ORGANISM: Artificial Sequence
<220> FEATURE:
<223> OTHER INFORMATION: fustion protein

<400> SEQUENCE: 168

Pro Asp Gly Lys Lys Gly Glu Ala Gly Arg Pro Gly Arg Arg Gly Arg
1               5                   10                  15

Pro Gly

<210> SEQ ID NO 169
<211> LENGTH: 18
<212> TYPE: PRT
<213> ORGANISM: Artificial Sequence
<220> FEATURE:
<223> OTHER INFORMATION: fusion protein
```

<400> SEQUENCE: 169

Asp Gly Lys Lys Gly Glu Ala Gly Arg Pro Gly Arg Arg Gly Arg Pro
1               5                   10                  15

Gly Leu

<210> SEQ ID NO 170
<211> LENGTH: 18
<212> TYPE: PRT
<213> ORGANISM: Artificial Sequence
<220> FEATURE:
<223> OTHER INFORMATION: fusion protein

<400> SEQUENCE: 170

Gly Lys Lys Gly Glu Ala Gly Arg Pro Gly Arg Arg Gly Arg Pro Gly
1               5                   10                  15

Leu Lys

<210> SEQ ID NO 171
<211> LENGTH: 18
<212> TYPE: PRT
<213> ORGANISM: Artificial Sequence
<220> FEATURE:
<223> OTHER INFORMATION: fusion protein

<400> SEQUENCE: 171

Lys Lys Gly Glu Ala Gly Arg Pro Gly Arg Arg Gly Arg Pro Gly Leu
1               5                   10                  15

Lys Gly

<210> SEQ ID NO 172
<211> LENGTH: 18
<212> TYPE: PRT
<213> ORGANISM: Artificial Sequence
<220> FEATURE:
<223> OTHER INFORMATION: fusion protein

<400> SEQUENCE: 172

Lys Gly Glu Ala Gly Arg Pro Gly Arg Arg Gly Arg Pro Gly Leu Lys
1               5                   10                  15

Gly Glu

<210> SEQ ID NO 173
<211> LENGTH: 18
<212> TYPE: PRT
<213> ORGANISM: Artificial Sequence
<220> FEATURE:
<223> OTHER INFORMATION: fusion protein

<400> SEQUENCE: 173

Gly Glu Ala Gly Arg Pro Gly Arg Arg Gly Arg Pro Gly Leu Lys Gly
1               5                   10                  15

Glu Gln

<210> SEQ ID NO 174
<211> LENGTH: 18
<212> TYPE: PRT
<213> ORGANISM: Artificial Sequence
<220> FEATURE:
<223> OTHER INFORMATION: fusion protein

<400> SEQUENCE: 174

Glu Ala Gly Arg Pro Gly Arg Arg Gly Arg Pro Gly Leu Lys Gly Glu

```
1               5                   10                  15

Gln Gly

<210> SEQ ID NO 175
<211> LENGTH: 17
<212> TYPE: PRT
<213> ORGANISM: Artificial Sequence
<220> FEATURE:
<223> OTHER INFORMATION: fusion protein

<400> SEQUENCE: 175

Asp Leu Cys Arg Ala Pro Asp Gly Lys Lys Gly Glu Ala Gly Arg Pro
1               5                   10                  15

Gly

<210> SEQ ID NO 176
<211> LENGTH: 17
<212> TYPE: PRT
<213> ORGANISM: Artificial Sequence
<220> FEATURE:
<223> OTHER INFORMATION: fusion protein

<400> SEQUENCE: 176

Leu Cys Arg Ala Pro Asp Gly Lys Lys Gly Glu Ala Gly Arg Pro Gly
1               5                   10                  15

Arg

<210> SEQ ID NO 177
<211> LENGTH: 17
<212> TYPE: PRT
<213> ORGANISM: Artificial Sequence
<220> FEATURE:
<223> OTHER INFORMATION: fusion protein

<400> SEQUENCE: 177

Cys Arg Ala Pro Asp Gly Lys Lys Gly Glu Ala Gly Arg Pro Gly Arg
1               5                   10                  15

Arg

<210> SEQ ID NO 178
<211> LENGTH: 17
<212> TYPE: PRT
<213> ORGANISM: Artificial Sequence
<220> FEATURE:
<223> OTHER INFORMATION: fusion protein

<400> SEQUENCE: 178

Arg Ala Pro Asp Gly Lys Lys Gly Glu Ala Gly Arg Pro Gly Arg Arg
1               5                   10                  15

Gly

<210> SEQ ID NO 179
<211> LENGTH: 17
<212> TYPE: PRT
<213> ORGANISM: Artificial Sequence
<220> FEATURE:
<223> OTHER INFORMATION: fusion protein

<400> SEQUENCE: 179

Ala Pro Asp Gly Lys Lys Gly Glu Ala Gly Arg Pro Gly Arg Arg Gly
1               5                   10                  15

Arg
```

<210> SEQ ID NO 180
<211> LENGTH: 17
<212> TYPE: PRT
<213> ORGANISM: Artificial Sequence
<220> FEATURE:
<223> OTHER INFORMATION: fusion protein

<400> SEQUENCE: 180

Pro Asp Gly Lys Lys Gly Glu Ala Gly Arg Pro Gly Arg Arg Gly Arg
1               5                   10                  15

Pro

<210> SEQ ID NO 181
<211> LENGTH: 17
<212> TYPE: PRT
<213> ORGANISM: Artificial Sequence
<220> FEATURE:
<223> OTHER INFORMATION: fusion protein

<400> SEQUENCE: 181

Asp Gly Lys Lys Gly Glu Ala Gly Arg Pro Gly Arg Arg Gly Arg Pro
1               5                   10                  15

Gly

<210> SEQ ID NO 182
<211> LENGTH: 17
<212> TYPE: PRT
<213> ORGANISM: Artificial Sequence
<220> FEATURE:
<223> OTHER INFORMATION: fusion protein

<400> SEQUENCE: 182

Gly Lys Lys Gly Glu Ala Gly Arg Pro Gly Arg Arg Gly Arg Pro Gly
1               5                   10                  15

Leu

<210> SEQ ID NO 183
<211> LENGTH: 17
<212> TYPE: PRT
<213> ORGANISM: Artificial Sequence
<220> FEATURE:
<223> OTHER INFORMATION: fusion protein

<400> SEQUENCE: 183

Lys Lys Gly Glu Ala Gly Arg Pro Gly Arg Arg Gly Arg Pro Gly Leu
1               5                   10                  15

Lys

<210> SEQ ID NO 184
<211> LENGTH: 17
<212> TYPE: PRT
<213> ORGANISM: Artificial Sequence
<220> FEATURE:
<223> OTHER INFORMATION: fusion protein

<400> SEQUENCE: 184

Lys Gly Glu Ala Gly Arg Pro Gly Arg Arg Gly Arg Pro Gly Leu Lys
1               5                   10                  15

Gly

<210> SEQ ID NO 185
<211> LENGTH: 17
<212> TYPE: PRT

```
<213> ORGANISM: Artificial Sequence
<220> FEATURE:
<223> OTHER INFORMATION: fusion protein

<400> SEQUENCE: 185

Gly Glu Ala Gly Arg Pro Gly Arg Arg Gly Arg Pro Gly Leu Lys Gly
1               5                   10                  15
Glu

<210> SEQ ID NO 186
<211> LENGTH: 17
<212> TYPE: PRT
<213> ORGANISM: Artificial Sequence
<220> FEATURE:
<223> OTHER INFORMATION: fusion protein

<400> SEQUENCE: 186

Glu Ala Gly Arg Pro Gly Arg Arg Gly Arg Pro Gly Leu Lys Gly Glu
1               5                   10                  15
Gln

<210> SEQ ID NO 187
<211> LENGTH: 16
<212> TYPE: PRT
<213> ORGANISM: Artificial Sequence
<220> FEATURE:
<223> OTHER INFORMATION: fusion protein

<400> SEQUENCE: 187

Leu Cys Arg Ala Pro Asp Gly Lys Lys Gly Glu Ala Gly Arg Pro Gly
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: fusion protein

<400> SEQUENCE: 188

Cys Arg Ala Pro Asp Gly Lys Lys Gly Glu Ala Gly Arg Pro Gly Arg
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: fusion protein

<400> SEQUENCE: 189

Arg Ala Pro Asp Gly Lys Lys Gly Glu Ala Gly Arg Pro Gly Arg Arg
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: fusion protein

<400> SEQUENCE: 190

Ala Pro Asp Gly Lys Lys Gly Glu Ala Gly Arg Pro Gly Arg Arg Gly
1               5                   10                  15
```

```
<210> SEQ ID NO 191
<211> LENGTH: 16
<212> TYPE: PRT
<213> ORGANISM: Artificial Sequence
<220> FEATURE:
<223> OTHER INFORMATION: fusion protein

<400> SEQUENCE: 191

Pro Asp Gly Lys Lys Gly Glu Ala Gly Arg Pro Gly Arg Arg Gly Arg
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: fusion protein

<400> SEQUENCE: 192

Asp Gly Lys Lys Gly Glu Ala Gly Arg Pro Gly Arg Arg Gly Arg Pro
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: fusion protein

<400> SEQUENCE: 193

Gly Lys Lys Gly Glu Ala Gly Arg Pro Gly Arg Arg Gly Arg Pro Gly
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: fusion protein

<400> SEQUENCE: 194

Lys Lys Gly Glu Ala Gly Arg Pro Gly Arg Arg Gly Arg Pro Gly Leu
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: fusion protein

<400> SEQUENCE: 195

Lys Gly Glu Ala Gly Arg Pro Gly Arg Arg Gly Arg Pro Gly Leu Lys
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: fusion protein

<400> SEQUENCE: 196

Gly Glu Ala Gly Arg Pro Gly Arg Arg Gly Arg Pro Gly Leu Lys Gly
1               5                   10                  15

<210> SEQ ID NO 197
```

```
<211> LENGTH: 16
<212> TYPE: PRT
<213> ORGANISM: Artificial Sequence
<220> FEATURE:
<223> OTHER INFORMATION: fusion protein

<400> SEQUENCE: 197

Glu Ala Gly Arg Pro Gly Arg Arg Gly Arg Pro Gly Leu Lys Gly Glu
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: fusion protein

<400> SEQUENCE: 198

Cys Arg Ala Pro Asp Gly Lys Lys Gly Glu Ala Gly Arg Pro Gly
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: fusion protein

<400> SEQUENCE: 199

Arg Ala Pro Asp Gly Lys Lys Gly Glu Ala Gly Arg Pro Gly Arg
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: fusion protein

<400> SEQUENCE: 200

Ala Pro Asp Gly Lys Lys Gly Glu Ala Gly Arg Pro Gly Arg Arg
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: fusion protein

<400> SEQUENCE: 201

Pro Asp Gly Lys Lys Gly Glu Ala Gly Arg Pro Gly Arg Arg Gly
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: fusion protein

<400> SEQUENCE: 202

Asp Gly Lys Lys Gly Glu Ala Gly Arg Pro Gly Arg Arg Gly Arg
1               5                   10                  15

<210> SEQ ID NO 203
<211> LENGTH: 15
```

```
<212> TYPE: PRT
<213> ORGANISM: Artificial Sequence
<220> FEATURE:
<223> OTHER INFORMATION: fusion protein

<400> SEQUENCE: 203

Gly Lys Lys Gly Glu Ala Gly Arg Pro Gly Arg Arg Gly Arg Pro
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: fusion protein

<400> SEQUENCE: 204

Lys Lys Gly Glu Ala Gly Arg Pro Gly Arg Arg Gly Arg Pro Gly
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: fusion protein

<400> SEQUENCE: 205

Lys Gly Glu Ala Gly Arg Pro Gly Arg Arg Gly Arg Pro Gly Leu
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: fusion protein

<400> SEQUENCE: 206

Gly Glu Ala Gly Arg Pro Gly Arg Arg Gly Arg Pro Gly Leu Lys
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: fusion protein

<400> SEQUENCE: 207

Glu Ala Gly Arg Pro Gly Arg Arg Gly Arg Pro Gly Leu Lys Gly
1               5                   10                  15

<210> SEQ ID NO 208
<211> LENGTH: 14
<212> TYPE: PRT
<213> ORGANISM: Artificial Sequence
<220> FEATURE:
<223> OTHER INFORMATION: fusion protein

<400> SEQUENCE: 208

Arg Ala Pro Asp Gly Lys Lys Gly Glu Ala Gly Arg Pro Gly
1               5                   10

<210> SEQ ID NO 209
<211> LENGTH: 14
<212> TYPE: PRT
```

<213> ORGANISM: Artificial Sequence
<220> FEATURE:
<223> OTHER INFORMATION: fusion protein

<400> SEQUENCE: 209

Ala Pro Asp Gly Lys Lys Gly Glu Ala Gly Arg Pro Gly Arg
1               5                   10

<210> SEQ ID NO 210
<211> LENGTH: 14
<212> TYPE: PRT
<213> ORGANISM: Artificial Sequence
<220> FEATURE:
<223> OTHER INFORMATION: fusion protein

<400> SEQUENCE: 210

Pro Asp Gly Lys Lys Gly Glu Ala Gly Arg Pro Gly Arg Arg
1               5                   10

<210> SEQ ID NO 211
<211> LENGTH: 14
<212> TYPE: PRT
<213> ORGANISM: Artificial Sequence
<220> FEATURE:
<223> OTHER INFORMATION: fusion protein

<400> SEQUENCE: 211

Asp Gly Lys Lys Gly Glu Ala Gly Arg Pro Gly Arg Arg Gly
1               5                   10

<210> SEQ ID NO 212
<211> LENGTH: 14
<212> TYPE: PRT
<213> ORGANISM: Artificial Sequence
<220> FEATURE:
<223> OTHER INFORMATION: fusion protein

<400> SEQUENCE: 212

Gly Lys Lys Gly Glu Ala Gly Arg Pro Gly Arg Arg Gly Arg
1               5                   10

<210> SEQ ID NO 213
<211> LENGTH: 14
<212> TYPE: PRT
<213> ORGANISM: Artificial Sequence
<220> FEATURE:
<223> OTHER INFORMATION: fusion protein

<400> SEQUENCE: 213

Lys Lys Gly Glu Ala Gly Arg Pro Gly Arg Arg Gly Arg Pro
1               5                   10

<210> SEQ ID NO 214
<211> LENGTH: 14
<212> TYPE: PRT
<213> ORGANISM: Artificial Sequence
<220> FEATURE:
<223> OTHER INFORMATION: fusion protein

<400> SEQUENCE: 214

Lys Gly Glu Ala Gly Arg Pro Gly Arg Arg Gly Arg Pro Gly
1               5                   10

<210> SEQ ID NO 215
<211> LENGTH: 14
<212> TYPE: PRT
<213> ORGANISM: Artificial Sequence
<220> FEATURE:
<223> OTHER INFORMATION: fusion protein

<400> SEQUENCE: 215

Gly Glu Ala Gly Arg Pro Gly Arg Arg Gly Arg Pro Gly Leu
1               5                   10

<210> SEQ ID NO 216
<211> LENGTH: 14
<212> TYPE: PRT
<213> ORGANISM: Artificial Sequence
<220> FEATURE:
<223> OTHER INFORMATION: fusion protein

<400> SEQUENCE: 216

Glu Ala Gly Arg Pro Gly Arg Arg Gly Arg Pro Gly Leu Lys
1               5                   10

<210> SEQ ID NO 217
<211> LENGTH: 13
<212> TYPE: PRT
<213> ORGANISM: Artificial Sequence
<220> FEATURE:
<223> OTHER INFORMATION: fusion protein

<400> SEQUENCE: 217

Ala Pro Asp Gly Lys Lys Gly Glu Ala Gly Arg Pro Gly
1               5                   10

<210> SEQ ID NO 218
<211> LENGTH: 13
<212> TYPE: PRT
<213> ORGANISM: Artificial Sequence
<220> FEATURE:
<223> OTHER INFORMATION: fusion protein

<400> SEQUENCE: 218

Pro Asp Gly Lys Lys Gly Glu Ala Gly Arg Pro Gly Arg
1               5                   10

<210> SEQ ID NO 219
<211> LENGTH: 13
<212> TYPE: PRT
<213> ORGANISM: Artificial Sequence
<220> FEATURE:
<223> OTHER INFORMATION: fusion protein

<400> SEQUENCE: 219

Asp Gly Lys Lys Gly Glu Ala Gly Arg Pro Gly Arg Arg
1               5                   10

<210> SEQ ID NO 220
<211> LENGTH: 13
<212> TYPE: PRT
<213> ORGANISM: Artificial Sequence
<220> FEATURE:
<223> OTHER INFORMATION: fusion protein

<400> SEQUENCE: 220

Gly Lys Lys Gly Glu Ala Gly Arg Pro Gly Arg Arg Gly
1               5                   10

<210> SEQ ID NO 221
<211> LENGTH: 13
<212> TYPE: PRT
<213> ORGANISM: Artificial Sequence
<220> FEATURE:

<223> OTHER INFORMATION: fusion protein

<400> SEQUENCE: 221

Lys Lys Gly Glu Ala Gly Arg Pro Gly Arg Arg Gly Arg
1               5                   10

<210> SEQ ID NO 222
<211> LENGTH: 13
<212> TYPE: PRT
<213> ORGANISM: Artificial Sequence
<220> FEATURE:
<223> OTHER INFORMATION: fusion protein

<400> SEQUENCE: 222

Lys Gly Glu Ala Gly Arg Pro Gly Arg Arg Gly Arg Pro
1               5                   10

<210> SEQ ID NO 223
<211> LENGTH: 13
<212> TYPE: PRT
<213> ORGANISM: Artificial Sequence
<220> FEATURE:
<223> OTHER INFORMATION: fusion protein

<400> SEQUENCE: 223

Gly Glu Ala Gly Arg Pro Gly Arg Arg Gly Arg Pro Gly
1               5                   10

<210> SEQ ID NO 224
<211> LENGTH: 13
<212> TYPE: PRT
<213> ORGANISM: Artificial Sequence
<220> FEATURE:
<223> OTHER INFORMATION: fusion protein

<400> SEQUENCE: 224

Glu Ala Gly Arg Pro Gly Arg Arg Gly Arg Pro Gly Leu
1               5                   10

<210> SEQ ID NO 225
<211> LENGTH: 12
<212> TYPE: PRT
<213> ORGANISM: Artificial Sequence
<220> FEATURE:
<223> OTHER INFORMATION: fusion protein

<400> SEQUENCE: 225

Pro Asp Gly Lys Lys Gly Glu Ala Gly Arg Pro Gly
1               5                   10

<210> SEQ ID NO 226
<211> LENGTH: 12
<212> TYPE: PRT
<213> ORGANISM: Artificial Sequence
<220> FEATURE:
<223> OTHER INFORMATION: fusion protein

<400> SEQUENCE: 226

Asp Gly Lys Lys Gly Glu Ala Gly Arg Pro Gly Arg
1               5                   10

<210> SEQ ID NO 227
<211> LENGTH: 12
<212> TYPE: PRT
<213> ORGANISM: Artificial Sequence
<220> FEATURE:
<223> OTHER INFORMATION: fusion protein

```
<400> SEQUENCE: 227

Gly Lys Lys Gly Glu Ala Gly Arg Pro Gly Arg Arg
1               5                   10

<210> SEQ ID NO 228
<211> LENGTH: 12
<212> TYPE: PRT
<213> ORGANISM: Artificial Sequence
<220> FEATURE:
<223> OTHER INFORMATION: fusion protein

<400> SEQUENCE: 228

Lys Lys Gly Glu Ala Gly Arg Pro Gly Arg Arg Gly
1               5                   10

<210> SEQ ID NO 229
<211> LENGTH: 12
<212> TYPE: PRT
<213> ORGANISM: Artificial Sequence
<220> FEATURE:
<223> OTHER INFORMATION: fusion protein

<400> SEQUENCE: 229

Lys Gly Glu Ala Gly Arg Pro Gly Arg Arg Gly Arg
1               5                   10

<210> SEQ ID NO 230
<211> LENGTH: 12
<212> TYPE: PRT
<213> ORGANISM: Artificial Sequence
<220> FEATURE:
<223> OTHER INFORMATION: fusion protein

<400> SEQUENCE: 230

Gly Glu Ala Gly Arg Pro Gly Arg Arg Gly Arg Pro
1               5                   10

<210> SEQ ID NO 231
<211> LENGTH: 12
<212> TYPE: PRT
<213> ORGANISM: Artificial Sequence
<220> FEATURE:
<223> OTHER INFORMATION: fusion protein

<400> SEQUENCE: 231

Glu Ala Gly Arg Pro Gly Arg Arg Gly Arg Pro Gly
1               5                   10

<210> SEQ ID NO 232
<211> LENGTH: 11
<212> TYPE: PRT
<213> ORGANISM: Artificial Sequence
<220> FEATURE:
<223> OTHER INFORMATION: fusion protein

<400> SEQUENCE: 232

Asp Gly Lys Lys Gly Glu Ala Gly Arg Pro Gly
1               5                   10

<210> SEQ ID NO 233
<211> LENGTH: 11
<212> TYPE: PRT
<213> ORGANISM: Artificial Sequence
<220> FEATURE:
<223> OTHER INFORMATION: fusion protein
```

<400> SEQUENCE: 233

Gly Lys Lys Gly Glu Ala Gly Arg Pro Gly Arg
1               5                   10

<210> SEQ ID NO 234
<211> LENGTH: 11
<212> TYPE: PRT
<213> ORGANISM: Artificial Sequence
<220> FEATURE:
<223> OTHER INFORMATION: fusion protein

<400> SEQUENCE: 234

Lys Lys Gly Glu Ala Gly Arg Pro Gly Arg Arg
1               5                   10

<210> SEQ ID NO 235
<211> LENGTH: 11
<212> TYPE: PRT
<213> ORGANISM: Artificial Sequence
<220> FEATURE:
<223> OTHER INFORMATION: fusion protein

<400> SEQUENCE: 235

Lys Gly Glu Ala Gly Arg Pro Gly Arg Arg Gly
1               5                   10

<210> SEQ ID NO 236
<211> LENGTH: 11
<212> TYPE: PRT
<213> ORGANISM: Artificial Sequence
<220> FEATURE:
<223> OTHER INFORMATION: fusion protein

<400> SEQUENCE: 236

Gly Glu Ala Gly Arg Pro Gly Arg Arg Gly Arg
1               5                   10

<210> SEQ ID NO 237
<211> LENGTH: 11
<212> TYPE: PRT
<213> ORGANISM: Artificial Sequence
<220> FEATURE:
<223> OTHER INFORMATION: fusion protein

<400> SEQUENCE: 237

Glu Ala Gly Arg Pro Gly Arg Arg Gly Arg Pro
1               5                   10

<210> SEQ ID NO 238
<211> LENGTH: 10
<212> TYPE: PRT
<213> ORGANISM: Artificial Sequence
<220> FEATURE:
<223> OTHER INFORMATION: fusion protein

<400> SEQUENCE: 238

Gly Lys Lys Gly Glu Ala Gly Arg Pro Gly
1               5                   10

<210> SEQ ID NO 239
<211> LENGTH: 10
<212> TYPE: PRT
<213> ORGANISM: Artificial Sequence
<220> FEATURE:
<223> OTHER INFORMATION: fustion protein

<400> SEQUENCE: 239

```
Lys Lys Gly Glu Ala Gly Arg Pro Gly Arg
1               5                   10

<210> SEQ ID NO 240
<211> LENGTH: 10
<212> TYPE: PRT
<213> ORGANISM: Artificial Sequence
<220> FEATURE:
<223> OTHER INFORMATION: fusion protein

<400> SEQUENCE: 240

Lys Gly Glu Ala Gly Arg Pro Gly Arg Arg
1               5                   10

<210> SEQ ID NO 241
<211> LENGTH: 10
<212> TYPE: PRT
<213> ORGANISM: Artificial Sequence
<220> FEATURE:
<223> OTHER INFORMATION: fusion protein

<400> SEQUENCE: 241

Gly Glu Ala Gly Arg Pro Gly Arg Arg Gly
1               5                   10

<210> SEQ ID NO 242
<211> LENGTH: 10
<212> TYPE: PRT
<213> ORGANISM: Artificial Sequence
<220> FEATURE:
<223> OTHER INFORMATION: fusion protein

<400> SEQUENCE: 242

Glu Ala Gly Arg Pro Gly Arg Arg Gly Arg
1               5                   10

<210> SEQ ID NO 243
<211> LENGTH: 9
<212> TYPE: PRT
<213> ORGANISM: Artificial Sequence
<220> FEATURE:
<223> OTHER INFORMATION: fusion protein

<400> SEQUENCE: 243

Lys Lys Gly Glu Ala Gly Arg Pro Gly
1               5

<210> SEQ ID NO 244
<211> LENGTH: 9
<212> TYPE: PRT
<213> ORGANISM: Artificial Sequence
<220> FEATURE:
<223> OTHER INFORMATION: fusion protein

<400> SEQUENCE: 244

Lys Gly Glu Ala Gly Arg Pro Gly Arg
1               5

<210> SEQ ID NO 245
<211> LENGTH: 9
<212> TYPE: PRT
<213> ORGANISM: Artificial Sequence
<220> FEATURE:
<223> OTHER INFORMATION: fusion protein

<400> SEQUENCE: 245
```

Gly Glu Ala Gly Arg Pro Gly Arg Arg
1               5

<210> SEQ ID NO 246
<211> LENGTH: 9
<212> TYPE: PRT
<213> ORGANISM: Artificial Sequence
<220> FEATURE:
<223> OTHER INFORMATION: fusion protein

<400> SEQUENCE: 246

Glu Ala Gly Arg Pro Gly Arg Arg Gly
1               5

<210> SEQ ID NO 247
<211> LENGTH: 8
<212> TYPE: PRT
<213> ORGANISM: Artificial Sequence
<220> FEATURE:
<223> OTHER INFORMATION: fusion protein

<400> SEQUENCE: 247

Lys Gly Glu Ala Gly Arg Pro Gly
1               5

<210> SEQ ID NO 248
<211> LENGTH: 8
<212> TYPE: PRT
<213> ORGANISM: Artificial Sequence
<220> FEATURE:
<223> OTHER INFORMATION: fusion protein

<400> SEQUENCE: 248

Gly Glu Ala Gly Arg Pro Gly Arg
1               5

<210> SEQ ID NO 249
<211> LENGTH: 8
<212> TYPE: PRT
<213> ORGANISM: Artificial Sequence
<220> FEATURE:
<223> OTHER INFORMATION: fusion protein

<400> SEQUENCE: 249

Glu Ala Gly Arg Pro Gly Arg Arg
1               5

<210> SEQ ID NO 250
<211> LENGTH: 7
<212> TYPE: PRT
<213> ORGANISM: Artificial Sequence
<220> FEATURE:
<223> OTHER INFORMATION: fusion protein

<400> SEQUENCE: 250

Gly Glu Ala Gly Arg Pro Gly
1               5

<210> SEQ ID NO 251
<211> LENGTH: 7
<212> TYPE: PRT
<213> ORGANISM: Artificial Sequence
<220> FEATURE:
<223> OTHER INFORMATION: fusion protein

<400> SEQUENCE: 251

Glu Ala Gly Arg Pro Gly Arg

```
<210> SEQ ID NO 252
<211> LENGTH: 10
<212> TYPE: PRT
<213> ORGANISM: Artificial Sequence
<220> FEATURE:
<223> OTHER INFORMATION: peptide library

<400> SEQUENCE: 252

Trp Cys Glu Ala Asp Tyr Gly Arg Cys Pro
1               5                   10
```